US011470940B2

(12) United States Patent
Grez et al.

(10) Patent No.: US 11,470,940 B2
(45) Date of Patent: Oct. 18, 2022

(54) FORMULA DELIVERY DEVICE

(71) Applicant: L'Oreal, Paris (FR)

(72) Inventors: Joseph W. Grez, North Bend, WA (US); Carolina Canamaque, Clark, NJ (US); John Streeter, Redmond, WA (US); Richard Taylor, Fall City, WA (US); Mark E. Bartlett, North East, PA (US); Scott P. Mosby, Memphis, NY (US); Joseph Michael Recco, Spencerport, NY (US); Francis George Tatu, Minlius, NY (US); Adam Paul Vallee, Cato, NY (US)

(73) Assignee: L'OREAL, Paris (FR)

( * ) Notice: Subject to any disclaimer, the term of this patent is extended or adjusted under 35 U.S.C. 154(b) by 1056 days.

(21) Appl. No.: 15/721,659

(22) Filed: Sep. 29, 2017

(65) Prior Publication Data
US 2019/0098974 A1    Apr. 4, 2019

(51) Int. Cl.
A45D 24/28    (2006.01)
A45D 24/26    (2006.01)
(Continued)

(52) U.S. Cl.
CPC ........... *A45D 24/28* (2013.01); *A45D 24/007* (2013.01); *A45D 24/16* (2013.01); *A45D 24/26* (2013.01);
(Continued)

(58) Field of Classification Search
CPC .. A45D 19/02; A45D 2019/025; A45D 24/22; A45D 24/26; A45D 24/24; A45D 24/28
See application file for complete search history.

(56) References Cited

U.S. PATENT DOCUMENTS 1,190,017 A    7/1916  Scheel
1,615,581 A  *  1/1927  Harris ................... A45D 24/24
                                                      222/88
(Continued)

FOREIGN PATENT DOCUMENTS

CN     201452024 U    5/2010
CN     204635373 U    9/2015
(Continued)

OTHER PUBLICATIONS

International Preliminary Report on Patentability, dated Apr. 9, 2020, issued in corresponding Application No. PCT/US2018/052345, filed Sep. 24, 2018, 2 pages.
(Continued)

*Primary Examiner* — Cris L. Rodriguez
*Assistant Examiner* — Brianne E Kalach
(74) *Attorney, Agent, or Firm* — Christensen O'Connor Johnson Kindness PLLC

(57) ABSTRACT

A formula delivery system can be used in conjunction with hair and scalp treatment appliances to supply a hair treatment formulation to the appliance. In one aspect, the formula delivery system delivers hair coloring formulation to the appliance. Formula delivery systems of the present disclosure generally include at least one fluid container configured to retain a volume of formulation for delivery of the formulation to a hair coloring appliance. In this regard, the formula delivery system may be configured to removably couple to an inlet member of the appliance that allows the appliance to draw the formulation from the fluid container for use within the appliance.

24 Claims, 16 Drawing Sheets

(51) Int. Cl.
  *A45D 24/16* (2006.01)
  *A45D 24/00* (2006.01)
  *A61M 35/00* (2006.01)
  *A45D 19/00* (2006.01)

(52) U.S. Cl.
  CPC .. *A45D 19/0083* (2021.01); *A45D 2019/0033* (2013.01); *A61M 35/003* (2013.01)

(56) References Cited

U.S. PATENT DOCUMENTS

| | | | |
|---|---|---|---|
| 1,818,281 A * | 8/1931 | Soss | A46B 11/066 |
| | | | 15/22.1 |
| 2,272,641 A | 2/1942 | Mureau | |
| 2,799,881 A | 7/1957 | Howe | |
| 3,608,782 A * | 9/1971 | Sathicq | A45D 19/02 |
| | | | 222/94 |
| 3,688,782 A | 9/1972 | Smith | |
| 4,533,273 A | 8/1985 | Obata et al. | |
| 4,617,875 A | 10/1986 | Holland | |
| 4,704,226 A | 11/1987 | Naylor | |
| 4,792,250 A * | 12/1988 | Turner | A45D 19/16 |
| | | | 401/43 |
| 4,974,984 A | 12/1990 | Kafkis et al. | |
| 4,993,859 A | 2/1991 | Assad et al. | |
| 5,078,157 A | 1/1992 | Golan et al. | |
| 5,432,582 A | 7/1995 | Horning et al. | |
| 5,482,058 A | 1/1996 | Garconnet | |
| 5,526,957 A * | 6/1996 | Brown | B29B 7/7404 |
| | | | 222/96 |
| 5,839,451 A | 11/1998 | Dorber et al. | |
| 5,937,865 A | 8/1999 | Dhaliwal | |
| 6,022,163 A | 2/2000 | Asfur | |
| 6,145,513 A * | 11/2000 | Chu | A45D 19/02 |
| | | | 132/112 |
| 7,157,816 B2 | 1/2007 | Pilcher et al. | |
| 7,455,195 B2 * | 11/2008 | Mekata | B05B 11/3081 |
| | | | 222/94 |
| 7,481,592 B2 | 1/2009 | Gueret | |
| 7,722,277 B2 | 5/2010 | Byun | |
| 7,786,626 B2 | 8/2010 | Reishus et al. | |
| 7,794,168 B2 | 9/2010 | Chang | |
| 8,007,192 B2 | 8/2011 | Huang | |
| 8,220,469 B1 | 7/2012 | Spagnuolo | |
| 8,464,732 B2 | 6/2013 | Wong | |
| 8,506,193 B1 | 8/2013 | Zhang | |
| 9,211,756 B2 | 12/2015 | Ballot | |
| 9,364,068 B2 | 6/2016 | Kodama | |
| 9,462,873 B2 | 10/2016 | Casasanta, III | |
| 2003/0059247 A1 | 3/2003 | Kandasamy et al. | |
| 2004/0187883 A1* | 9/2004 | Shah | B01F 5/0657 |
| | | | 132/112 |
| 2005/0184091 A1 | 8/2005 | Abergel | |
| 2005/0199254 A1 | 9/2005 | Kang | |
| 2006/0021627 A1* | 2/2006 | Lee | A45D 19/02 |
| | | | 132/113 |
| 2006/0210352 A1 | 9/2006 | Clark | |
| 2008/0083845 A1 | 4/2008 | Lind et al. | |
| 2008/0106156 A1 | 5/2008 | Reishus et al. | |
| 2008/0167590 A1 | 7/2008 | Jon et al. | |
| 2008/0317544 A1 | 12/2008 | Spirk et al. | |
| 2008/0319446 A1 | 12/2008 | Young | |
| 2009/0014021 A1* | 1/2009 | Gayton | A45D 19/02 |
| | | | 132/200 |
| 2009/0016805 A1 | 1/2009 | Byun | |
| 2009/0020551 A1 | 1/2009 | Malvar et al. | |
| 2009/0097899 A1 | 4/2009 | Carroll | |
| 2009/0126752 A1* | 5/2009 | Emerson | A45D 24/22 |
| | | | 132/200 |
| 2009/0154985 A1 | 6/2009 | Wyatt et al. | |
| 2009/0180825 A1 | 7/2009 | Chang | |
| 2010/0132730 A1* | 6/2010 | Jung | A45D 19/02 |
| | | | 401/269 |
| 2011/0116857 A1 | 5/2011 | Carroll et al. | |
| 2011/0240766 A1 | 10/2011 | Peterson et al. | |
| 2012/0260931 A1 | 10/2012 | Martin et al. | |
| 2012/0328353 A1 | 12/2012 | Svendsen et al. | |
| 2013/0118515 A1 | 5/2013 | Wurtz et al. | |
| 2013/0123825 A1 | 5/2013 | Demjanenko | |
| 2013/0158547 A1 | 6/2013 | David | |
| 2013/0223915 A1 | 8/2013 | Simonian et al. | |
| 2014/0000047 A1 | 1/2014 | Boyd et al. | |
| 2014/0014543 A1 | 1/2014 | Hohlbein | |
| 2014/0064821 A1 | 3/2014 | Price et al. | |
| 2014/0219705 A1 | 8/2014 | Posnick | |
| 2014/0311509 A1* | 10/2014 | Antons | A45D 19/02 |
| | | | 132/112 |
| 2014/0360527 A1 | 12/2014 | Thompson | |
| 2015/0308421 A1 | 10/2015 | Vogt | |
| 2016/0015150 A1 | 1/2016 | Casasanta, III | |
| 2016/0143408 A1 | 5/2016 | Grez | |
| 2016/0166032 A1 | 6/2016 | Grez | |
| 2016/0183664 A1 | 6/2016 | Grez | |
| 2018/0116363 A1 | 5/2018 | Grez | |

FOREIGN PATENT DOCUMENTS

| | | | |
|---|---|---|---|
| EP | 1 459 782 A2 | | 9/2004 |
| EP | 1669139 A1 | | 6/2006 |
| EP | 2 211 235 A1 | | 7/2010 |
| EP | 3612313 A1 | | 2/2020 |
| EP | 3612314 A1 | | 2/2020 |
| FR | 2 992 856 A1 | | 1/2014 |
| JP | 61-139795 A | | 6/1986 |
| JP | 63-046976 U | | 3/1988 |
| JP | 2002326677 A | | 11/2002 |
| JP | 2003319835 A | | 11/2003 |
| JP | 2004-51122 A | | 2/2004 |
| JP | 2004155484 | * | 6/2004 |
| JP | 2004155484 A | | 6/2004 |
| JP | 2005126144 A | | 5/2005 |
| JP | 2005206230 A | | 8/2005 |
| JP | 2006069581 A | | 3/2006 |
| JP | 2007308181 A | | 11/2007 |
| JP | 2008-531083 A | | 8/2008 |
| JP | 2008237693 A | | 10/2008 |
| JP | 2011-502656 A | | 1/2011 |
| JP | 2013082478 A | | 5/2013 |
| JP | 2013-106741 A | | 6/2013 |
| KR | 10-1311142 B1 | | 9/2013 |
| WO | 2006/090998 A1 | | 8/2006 |
| WO | 2008023955 A1 | | 2/2008 |
| WO | 2008108565 A1 | | 9/2008 |
| WO | 2009/064762 A2 | | 5/2009 |
| WO | 2011/009282 A1 | | 1/2011 |
| WO | 2012150779 A2 | | 8/2012 |
| WO | 2013/096520 A1 | | 6/2013 |
| WO | 2014/009282 A2 | | 1/2014 |

OTHER PUBLICATIONS

Notification of Reasons for Refusal dated Sep. 27, 2018, issued in JP Application No. 2017-502249, filed Apr. 30, 2015, 7 pages.
International Search Report and Written Opinion dated Jun. 7, 2019, Issued in corresponding Application No. PCT/US2018/052345, filed Sep. 24, 2018, 31 pages. European Patent Office.
Invitation to Pay Additional Fees, dated Jan. 3, 2019, issued in corresponding Application No. PCT/US2018/052345 filed Sep. 24, 2018, 14 pages.
International Search Report and Written Opinion dated Oct. 7, 2015, issued in corresponding International Application No. PCT/US2015/028562, filed Apr. 30, 2015, 17 pages.
Invitation to Pay Additional Fees and Partial International Search dated Jul. 31, 2015, issued in corresponding International Application No. PCT/US2015/028562, filed Apr. 30, 2015, 5 pages.
Notification of Reasons for Refusal dated Feb. 6, 2018, issued in JP Application No. 2017-502249, filed Apr. 30, 2015, 9 pages.
First Office Action dated Dec. 31, 2020, for Chinese Patent Application No. 201880062406.9, filed Sep. 24, 2018.
Examination Report dated Mar. 5, 2021, for Indian Patent Application No. 20201706548, filed Apr. 16, 2020.

(56) References Cited

OTHER PUBLICATIONS

European Examination Report dated Jun. 10, 2021, issued in European Application No. 18786134.9, filed on Sep. 24, 2019, 76 pages.
Japanese Office Action dated Apr. 19, 2021, issued in corresponding Japanese Application No. 2020-517897, filed on Sep. 24, 2018, and its English translation thereof, 9 pages.
English Translation of Notice of Reasons for Refusal dated Dec. 6, 2021, issued in corresponding Japanese Application No. 2020-517897, filed on Sep. 24, 2018, 3 pages.
Office Action dated Jul. 4, 2022, issued in corresponding Japanese Application No. 2020-517897, filed Sep. 24, 2018 (5 pages).

* cited by examiner

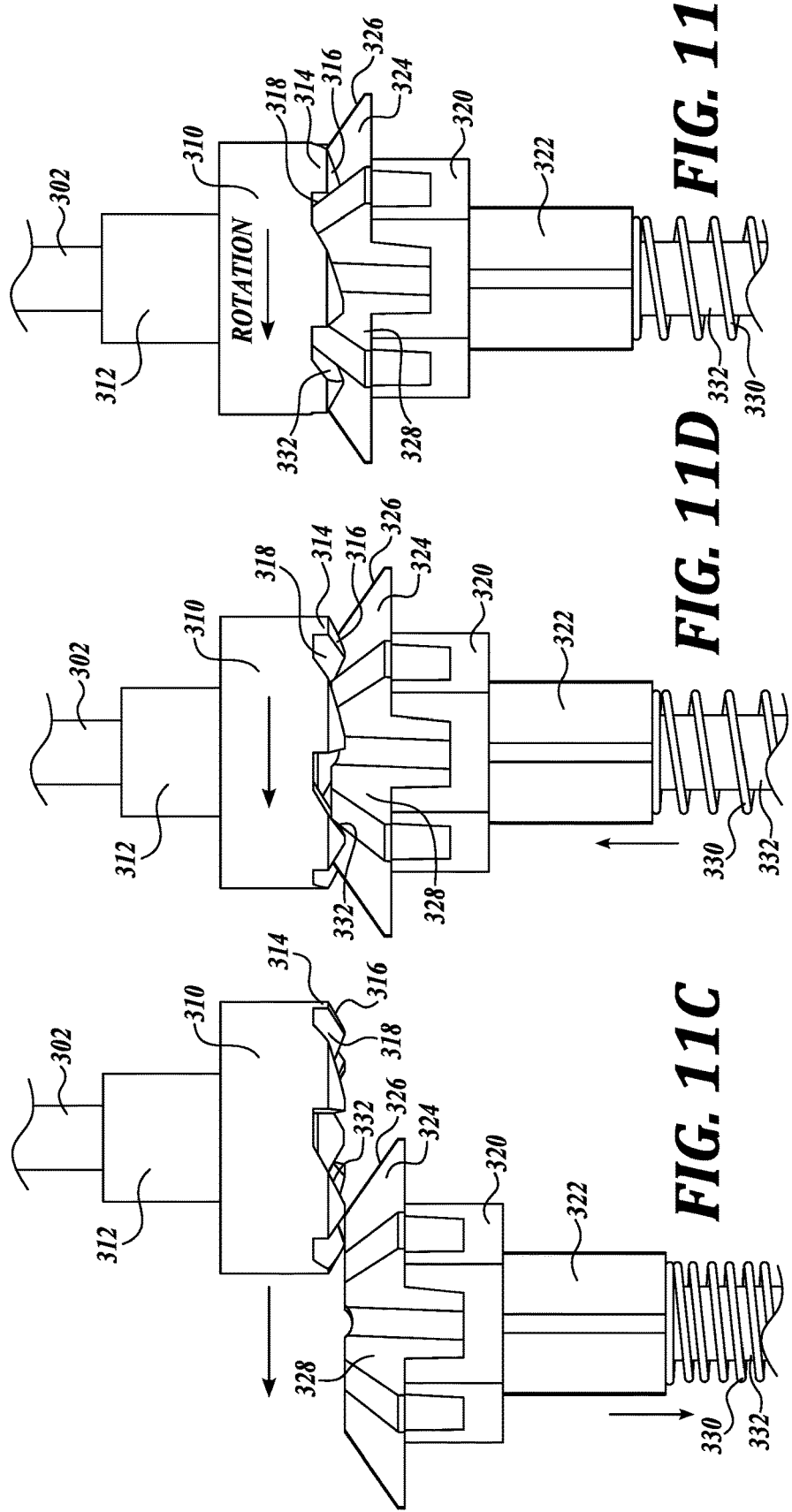

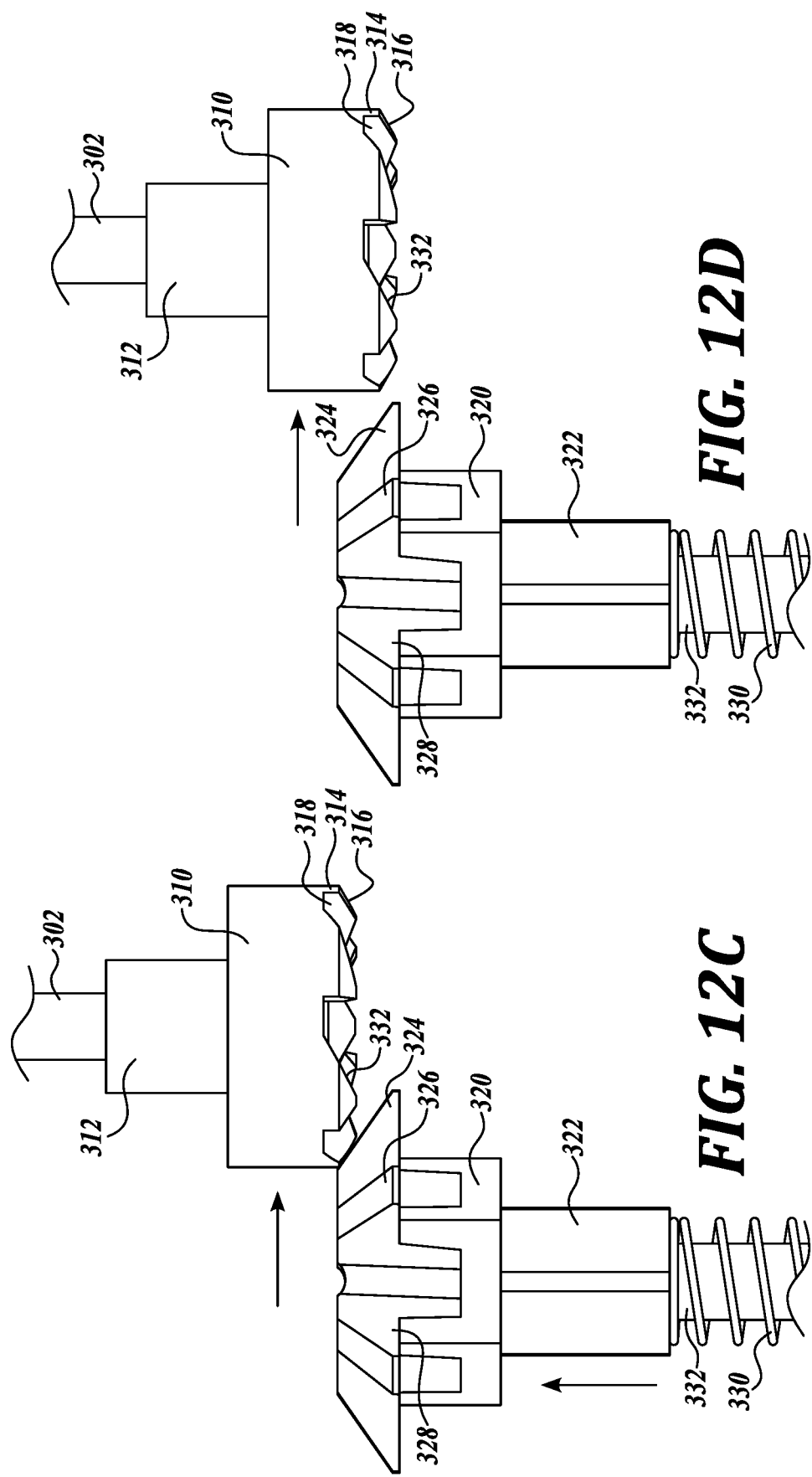

FORMULA DELIVERY DEVICE

CROSS-REFERENCES TO RELATED APPLICATIONS

This application is related to U.S. patent application Ser. Nos. 15/721,668, 15/721,678, and 15/721,682, filed Sep. 29, 2017, the entire disclosures of which are hereby incorporated by reference herein for all purposes.

SUMMARY

In an aspect, the present disclosure is directed to, among other things, representative embodiments of formula delivery systems and devices. The embodiments relate generally to hair and scalp treatment applicators and formulation delivery appliances. The formula delivery system generally includes at least one fluid container configured to retain a volume of formulation for delivery of the formulation to a hair coloring appliance. In this regard, the formula delivery system may be configured to removably couple to an inlet member that allows the appliance to draw the formulation from the fluid container for use within the appliance.

In accordance with one embodiment described herein, a formula delivery system is provided. The formula delivery system generally includes a fluid container configured to retain a volume of formulation, and a fluid receiving chamber having an inlet member, the fluid container removably couplable to the fluid receiving chamber such that upon coupling, the inlet member interfaces with an orifice of the fluid container to allow regulated flow of the formulation from the fluid container to the fluid receiving chamber.

In accordance with another embodiment described herein, a hair and scalp formulation delivery system is provided. The hair and scalp formulation delivery system generally includes a fluid container configured to retain a volume of formulation, a fluid receiving chamber having an inlet member, the fluid container removably couplable to the fluid receiving chamber such that upon coupling, the inlet member interfaces with an orifice of the fluid container to allow flow of the formulation from the fluid container to the fluid receiving chamber, a pump in fluid communication with the fluid receiving chamber to withdraw the formulation from the fluid container, and a formulation delivery nozzle in fluid communication with the pump configured to discharge the formulation from the delivery system.

In accordance with any of the embodiments described herein, the formula delivery system may further include a membrane covering the orifice.

In accordance with any of the embodiments described herein, the membrane may be pierceable by the inlet member upon coupling of the fluid container to the fluid receiving chamber.

In accordance with any of the embodiments described herein, the orifice may be configured for flow of the formulation into and out of the fluid container.

In accordance with any of the embodiments described herein, the fluid container may further comprise a valve configured to regulate the flow of the formulation out of the orifice.

In accordance with any of the embodiments described herein, the orifice may be closed until the fluid container is coupled to the fluid receiving chamber.

In accordance with any of the embodiments described herein, the fluid container may further comprise a membrane covering the orifice that is configured to allow outgassing of the formulation while substantially preventing the flow of formulation from the fluid chamber.

In accordance with any of the embodiments described herein, the fluid container may include a flexible wall that at least partially collapses as the formulation flows from the fluid chamber.

In accordance with any of the embodiments described herein, the fluid container may include a protrusion extending through the length of the fluid container, the protrusion configured to create a flow path for the formulation as the flexible wall at least partially collapses.

In accordance with any of the embodiments described herein, the fluid container may include a container shape that mates with a correspondingly shaped area of a housing for the fluid container.

In accordance with any of the embodiments described herein, the fluid container may include a flat wall such that the fluid container is rotationally oriented when inserted into the housing.

In accordance with any of the embodiments described herein, the fluid container may include a first internal bladder configured to retain a first formulation.

In accordance with any of the embodiments described herein, the fluid container may further include a second internal bladder configured to retain a second formulation.

In accordance with any of the embodiments described herein, the fluid receiving chamber may be configured to withdraw the formulation from the fluid container.

In accordance with any of the embodiments described herein, the formulation is selected from the group consisting of permanent hair dye, semi-permanent hair dye, developer, conditioner, hair growth treatment, ROGAINE®, hair protein treatment, disulfide bond repairing hair treatment, OLAPLEX®, fluid hair treatment, and fluid scalp treatment.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of the disclosed subject matter will become more readily appreciated as the same become better understood by reference to the following detailed description, when taken in conjunction with the accompanying drawings, wherein:

FIGS. 11A-11E are detailed side views of drive and driven gear assemblies of the appliance of FIG. 1, showing the gear assemblies moving from a non-engagement position to an engagement position;

FIGS. 12A-12D are detailed side views of the drive and driven gear assemblies of the appliance of FIG. 1, showing the gear assemblies moving from the engagement position to the non-engagement position;

DETAILED DESCRIPTION

Figure 1:
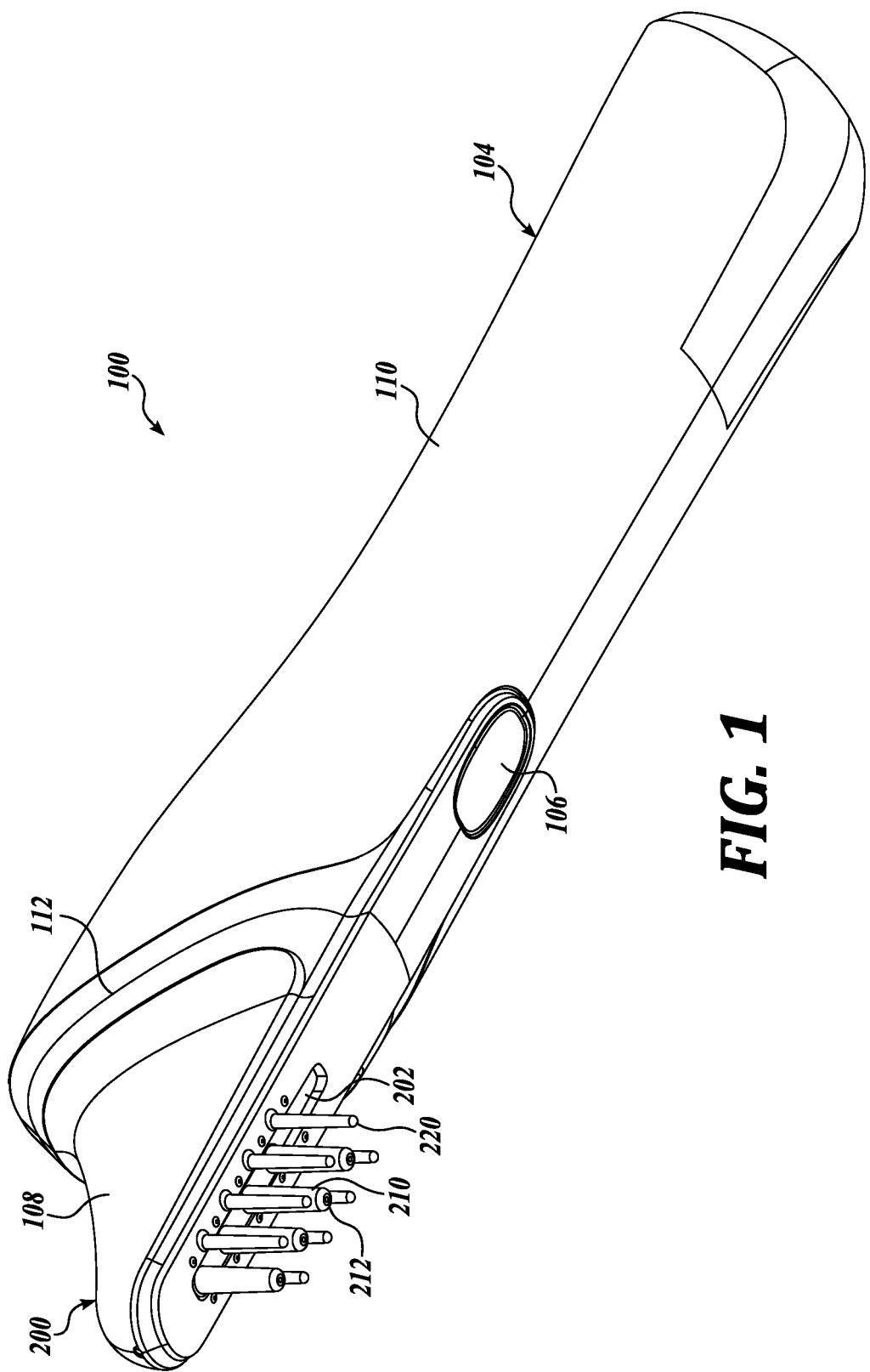
FIG. 1 is a first perspective view of one representative embodiment of a formulation delivery appliance in accordance with an aspect of the present disclosure.
Figure 2:
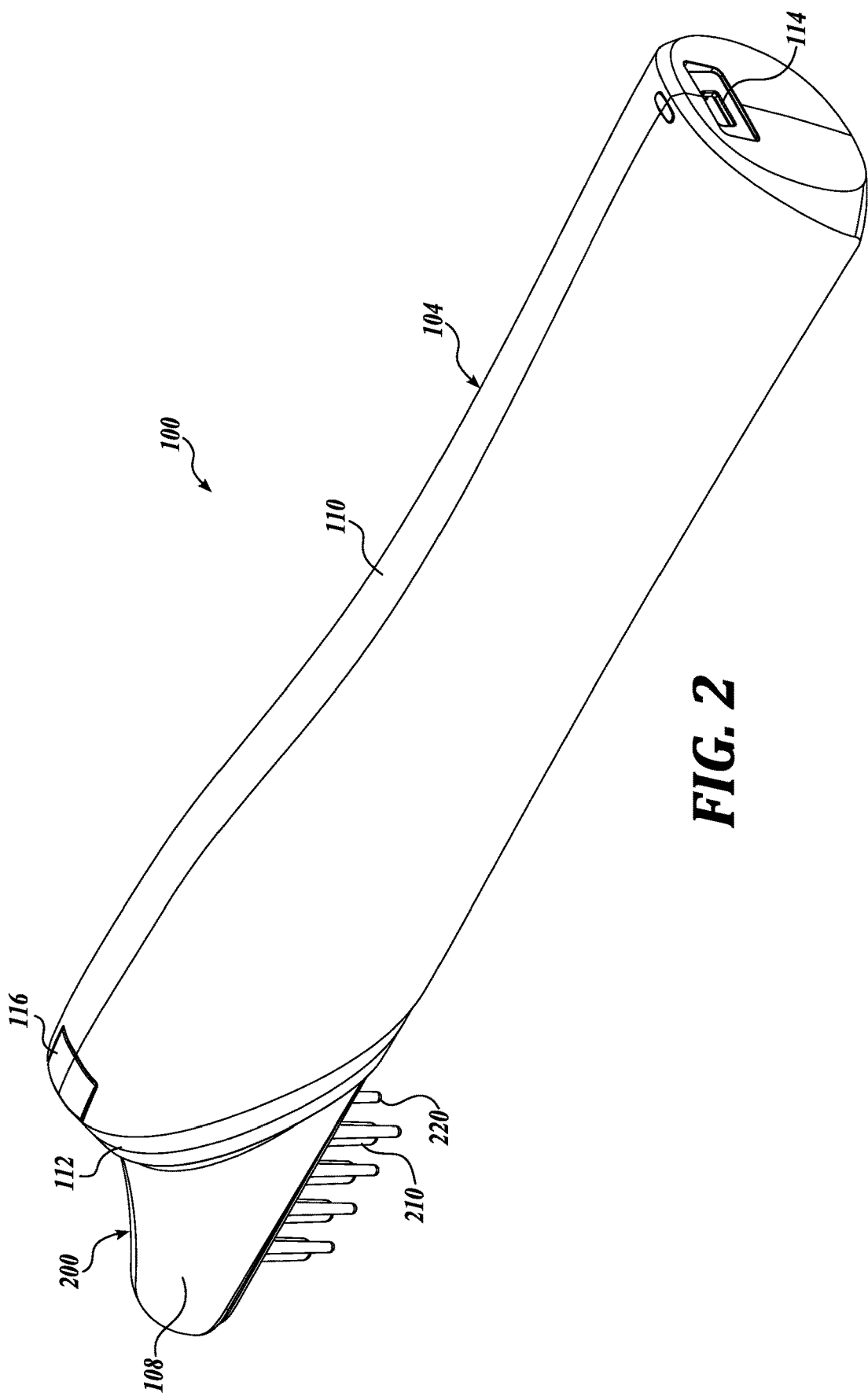
FIG. 2 is a second perspective view of the appliance of FIG. 1.

The following description provides several examples that relate generally to hair and scalp treatment applicators and formulation delivery appliances. Application of a wide variety of treatment formulations to human hair and scalp tissue is a common practice. In some instances, it is beneficial for the treatment formulation to be applied to a targeted portion of the hair or scalp tissue. In one example, applying a treatment formulation to a portion of the hair near the scalp may be desired, for instance, when applying a coloring dye to roots of hair during a color maintenance procedure. In another example, applying a treatment formulation directly to the scalp tissue, while minimizing contact with the hair, may be desired.

Existing systems for the application of hair and scalp treatment formulations have been widely used. In one example, hair coloring kits are generally used to change the appearance of the hair color or to blend gray hairs, among other uses. Existing hair coloring systems have several disadvantages, including difficulty of use, time consumption, uneven coverage, unpredictable results, excessive mess, etc. In one aspect, existing hair coloring systems can be ineffective in blending and coloring the roots of the hair after new segments of hair have grown from the scalp, where the natural hair color differs from the remainder of the dyed hair. The present disclosure is directed toward solving these and other needs.

Hair coloring formulation typically includes at least one dye and a separate developer, which must be mixed in controlled proportions for effective and predictable results. As used herein, the term "coloring formulation" (shown generally in FIGS. 14A and 14B as a coloring formulation CF) refers generally to any of the dye, developer, formulation, fluid, or any mixture thereof.

Embodiments of the present disclosure are configured to apply treatment formulation to targeted areas of the hair and scalp tissue. Examples of treatment formulations applied by the embodiments herein include: permanent hair dye; semi-permanent hair dye; developer; conditioner; hair growth treatment, such as minoxidil manufactured under the trade name ROGAINE®; hair protein treatment; disulfide bond repairing hair treatment, such as OLAPLEX®; fluid hair treatment; fluid scalp treatment, and the like. Although any hair and scalp treatment formulation is suitably applied using the embodiments of the appliance described herein, the present disclosure generally refers to hair coloring formulation as the example of treatment formulation applied by the appliance described below. However, it should be appreciated that any of the listed hair and scalp treatment formulations are interchangeable with the coloring formulation described herein.

Targeted coloring of the roots of the hair, such as during a maintenance procedure for previously colored hair, generally includes application of coloring formulation to hair segments near the scalp. To achieve the desired result of blending the segments of natural colored hair near the scalp with the previously colored hair, the coloring formulation generally should be applied to only the roots, requiring a precise delivery of coloring formulation.

The following discussion provides examples of systems, apparatuses, and/or appliances of a formula delivery device that is configured to apply treatment formulation to a targeted area of the hair and/or scalp. The appliance of the present disclosure generally includes a handle configured to be grasped by the hand of a user, and a head having a plurality of nozzles from which the coloring formulation is discharged. In some embodiments, the head may further include a plurality of standoff protrusions near the nozzles to space the orifice of the nozzle away from the scalp during use. In other embodiments, the nozzles may move during use, for example, by reciprocating or oscillating motion, such that the nozzles can deliver more thorough coverage of the treatment formulation.

Referring initially to FIGS. 1-4, an exemplary embodiment of a formula delivery device 100 for application of a coloring formulation to a user is depicted. The formula delivery device 100 is shown in use with a plurality of nozzles for implementing one or more methodologies or technologies such as, for example, applying a coloring formulation to the hair and/or scalp tissue of a user. For example, some coloring formulations have improved results when applied to a targeted area of the hair of the user, such as when treating the root segments of the hair, as described above. However, as also discussed above, conventional hair coloring kits are generally configured for manual mixing and application of the coloring formulation, a method of which is time consuming and not well-suited for consistent, desired results. In addition, results obtained from conventional hair coloring kits are often highly technique-dependent, requiring training and familiarity with the process for the desired results.

By use of the embodiments of the present disclosure, coloring formulation may be applied to portions of the hair in a way that would be difficult to accomplish with direct application of the coloring formulation alone. Embodiments of the present disclosure are also suitable for applying a treatment formulation to any surface of the body of the user or any other suitable surface.

Although the formula delivery device 100 and the other exemplary embodiments are described and illustrated as being used with a plurality of nozzles, it should be appreciated that the formula delivery devices shown and described herein may be used with any suitable formulation applicator configuration and for any suitable use.

Still referring to FIGS. 1-4, the formula delivery device 100 is shown as an appliance having a handle assembly 104 and a consumable assembly 200. In this regard, the formula delivery device 100 will be referred to hereinafter as an appliance 100. The handle assembly 104 includes a handle shell 110, a port 114, and a control button 106. The handle shell 110 provides a surface for a user to grasp with a hand while using the appliance 100. In this regard, the handle shell 110 is ergonomically shaped in the illustrated embodiments. However, in other embodiments, the handle shell 110 is suitably any shape to contain the internal components and provide one or more gripping surfaces for the user. In further embodiments, the consumable assembly 200 may form at least part of the gripping surfaces for the user.

The handle shell 110 houses various appliance control components, such as one or more of a drive motor having a drive gear 310 (see FIG. 3), a CPU, a battery, a communications system (such as wireless networking (Wi-Fi), Radio Frequency Identification (RFID), Near Field Communication (NFC), BLUETOOTH®, and the like), an electric and data connector at the port 114 (such as Universal Serial Bus (USB), Firewire, or the like), temperature sensors, accelerometers, fluid sensors, data scanners, light sources, audible signal generator, fluid heating sources, temperature controllers, and other suitable control components, which are not shown in the FIGURES for simplicity. In some embodiments, the port 114 is suitably used to provide an interface between the internal control components of the appliance 100 and external components/systems, and/or charge the battery of the appliance 100.

The control button 106 may be configured for the activating, deactivating, and controlling features of the appliance 100. In some embodiments, pressing the control button 106 powers on the appliance 100 such that coloring formulation CF is drawn from the formulation containers 424 (see FIGS. 14A and 14B). In these embodiments, releasing the control button 106 may stop the flow of coloring formulation CF. In certain examples, the control button 106 may be used to initialize the appliance 100 or place the appliance 100 in a state to perform certain functions, such as one or more of: calculating a mixture ratio of the components of the coloring formulation CF; entering a cleaning or purging mode; heating the formulation; gathering data from the formulation containers, such as volume remaining, mixture ratios, color information, etc.; sending and receiving signals through the port 114; analyzing data regarding user preferences; gathering data from sensors; providing status indication to the user, such as power output level, battery life, formulation volume remaining, sensor data, data connection information, etc.; and communicating with auxiliary equipment. In some embodiments, the control button 106 is capable of pressure sensitive operation, such that applying a higher pressure to the control button 106 causes a variable response, such as, for example, causing the formulation to flow faster, the nozzles to move faster, or the like. In some embodiments, various operating parameters can be controlled by the use of a smart device, such as a phone (as described in detail in U.S. patent application Ser. No. 14/586,138, which is incorporated by reference herein).

Figure 3:
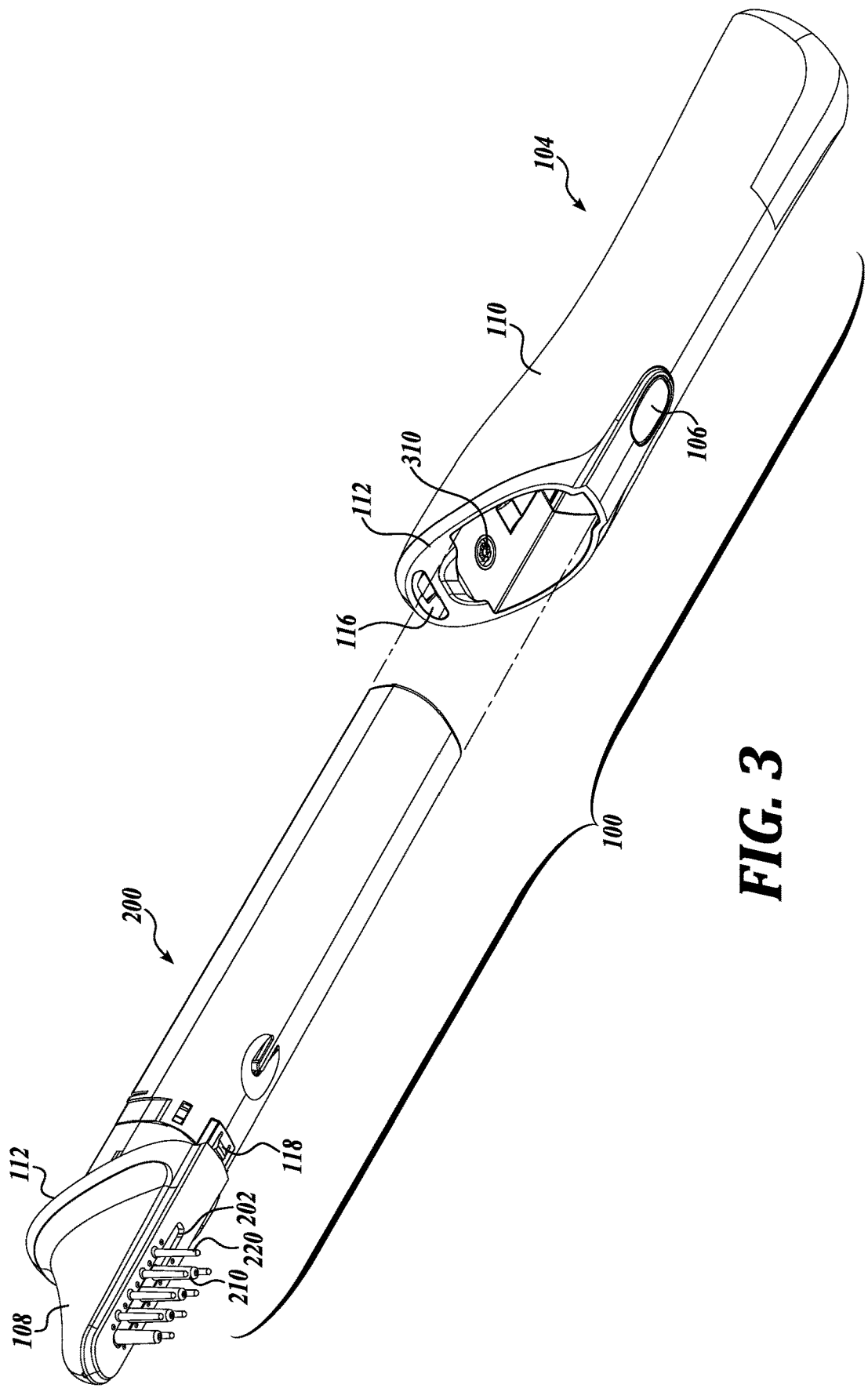
FIG. 3 is a first exploded perspective view of the appliance of FIG. 1, showing a consumable assembly and a handle assembly.
Figure 4:
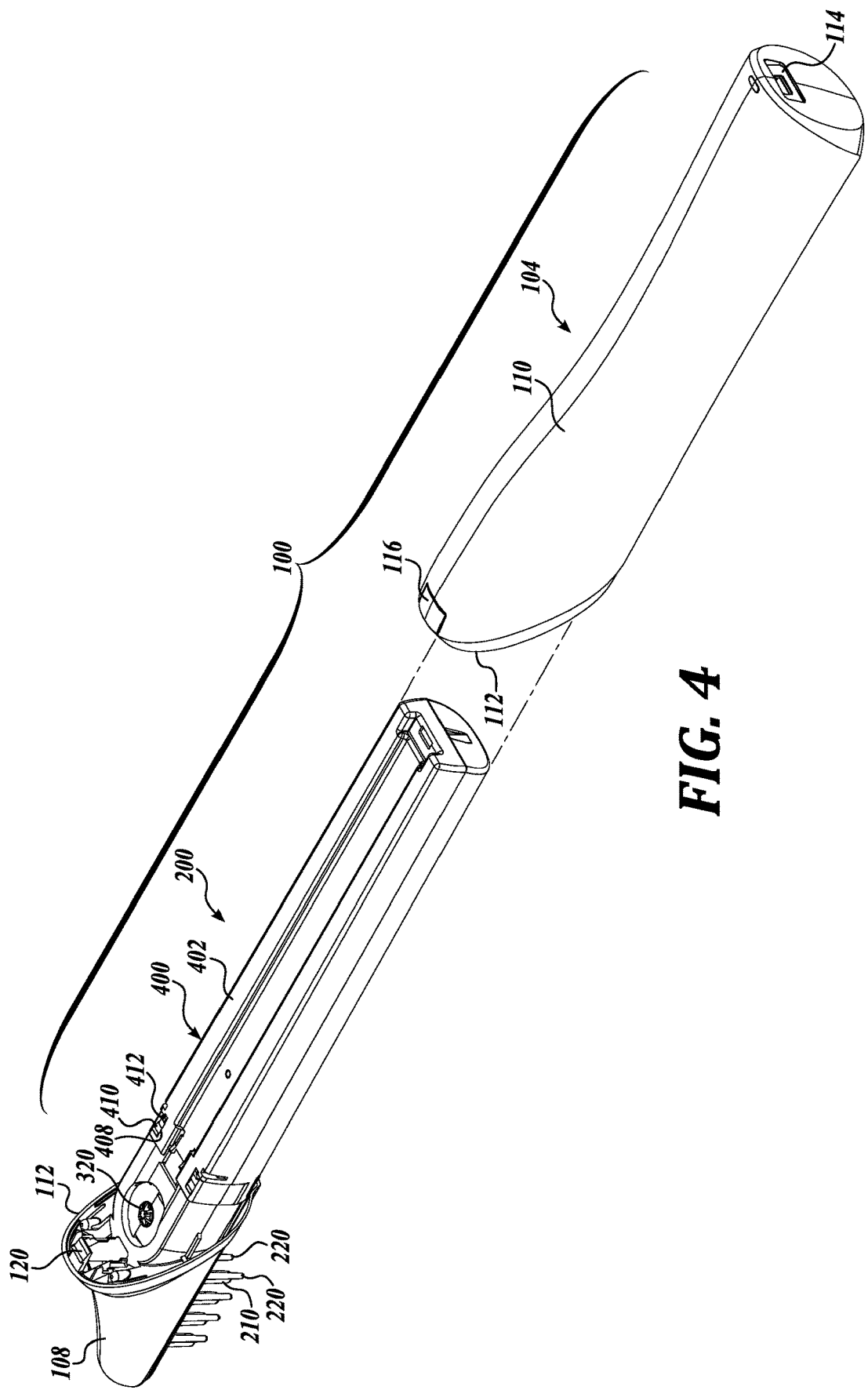
FIG. 4 is a second exploded perspective view of the appliance of FIG. 1, showing the consumable assembly and the handle assembly.

As shown in FIGS. 3 and 4, the consumable assembly 200 is removably joined with the handle assembly 104 to form the appliance 100. The external junction of the consumable assembly 200 and the handle assembly 104 is located at the parting surfaces 112 on each assembly. The parting surfaces 112 are generally configured to mate together forming a minimal gap such that fluid, dirt, debris, and other matter does not ingress the appliance 100. In some embodiments, the parting surfaces 112 mate together in a substantially flush configuration such that no sharp edges exist for ergonomic comfort to the user. Alternatively, in other embodiments, the handle shell 110 may be cut away so the consumable assembly 200 forms at least a portion of the gripping surfaces.

In the illustrated embodiments, to release and remove the consumable assembly 200 from the handle assembly 104, a release button 116 (see FIG. 4) may be pressed to release the grip of a consumable assembly detent feature 120 from the release button 116. In other embodiments, other securing configurations are suitably used, such as press-fit, fasteners, hook and loop, releasable adhesive, magnets, and the like. Additional securement features are also within the scope of the present disclosure, such as a lower detent 118, which may provide a greater securement force between the consumable assembly 200 and the handle assembly 104. In other embodiments, any number or combination of securement features are suitably used to secure the consumable assembly 200 to the handle assembly 104.

The consumable assembly 200 will now be described in greater detail. The consumable assembly 200 generally includes a head cover 108 to house and enclose various components of the consumable assembly 200, which will be described in greater detail below. The output area of the head cover 108 includes a plurality of elongate nozzles 210 extending from a manifold housing 202 coupled to or formed on the head cover 108. The elongate nozzles 210 are configured to discharge the coloring formulation CF through a plurality of outlet apertures 212 in the end of the nozzle 210 upon use of the appliance 100. In some embodiments, the nozzles 210 are arranged in one or more rows along the length of the head cover 108, generally in a direction along the length of the appliance 100, as shown in the FIGURES. In other embodiments, the nozzles 210 are suitably placed at an angle with respect to the length of the appliance 100.

In some embodiments, the nozzles 210 have a length between about 0.5 cm and about 4.0 cm from the manifold housing 202 to the end of the nozzles 210 at the outlet apertures 212. In other embodiments, the nozzles 210 have a length between about 1.4 cm and about 1.8 cm from the manifold housing 202 to the end of the nozzles 210 at the outlet apertures 212. In other embodiments, the nozzles 210 have a length of about 1.6 cm from the manifold housing 202 to the end of the nozzles 210 at the outlet apertures 212. In further embodiments, any length of nozzle is suitably used.

In the illustrated embodiment, a plurality of standoff protrusions 220 extend outwardly substantially in the direction of the nozzles 210 from the head cover 108 in one or more rows. In this regard, substantially in the direction of the nozzles 210 is intended to refer to within and angle of about 25 degrees of the direction along the length of the nozzles 210. In the depicted embodiment, first and second rows of protrusions 220 are positioned along each side of a single row of elongate nozzles 210. In some embodiments, the standoff protrusions 220 may be disposed at an angle relative to the plurality of nozzles 210. (For example, see FIG. 4 of U.S. patent application Ser. No. 15/339,551, which is incorporated by reference herein.)

In some embodiments, each of the standoff protrusions 220 has a length (measuring between the head cover 108 to an end of the standoff protrusion 220) such that the end of the standoff protrusion 220 and the outlet apertures 212 of the nozzles 210 is substantially coplanar. In other embodiments, the standoff protrusions 220 have a length (from the head cover 108 to the end of the standoff protrusion 220) such that the standoff protrusions 220 are longer than a length of the nozzles 210 (measuring between the head cover 108 to an end of the nozzles 210). In this regard, during use, the standoff protrusions 220 would contact an application surface, such as a localized portion of the scalp, and space the outlet aperture 212 of the nozzles 210 away from the application surface to provide a gap for discharge of the coloring formulation CF through the outlet aperture 212 (see, for example, height difference x in FIG. 7). In the embodiments where the standoff protrusions 220 are longer than the plurality of nozzles 210, the standoff protrusions 220 are between about 0.1 mm and 5.0 mm longer than the length of each of the plurality of nozzles 210. In other embodiments, the standoff protrusions 220 are between about 0.5 mm and 1.5 mm longer than the length of each of the plurality of nozzles 210. In other embodiments, the standoff protrusions 220 are about 1.0 mm longer than the length of each of the plurality of nozzles 210.

Figure 5:
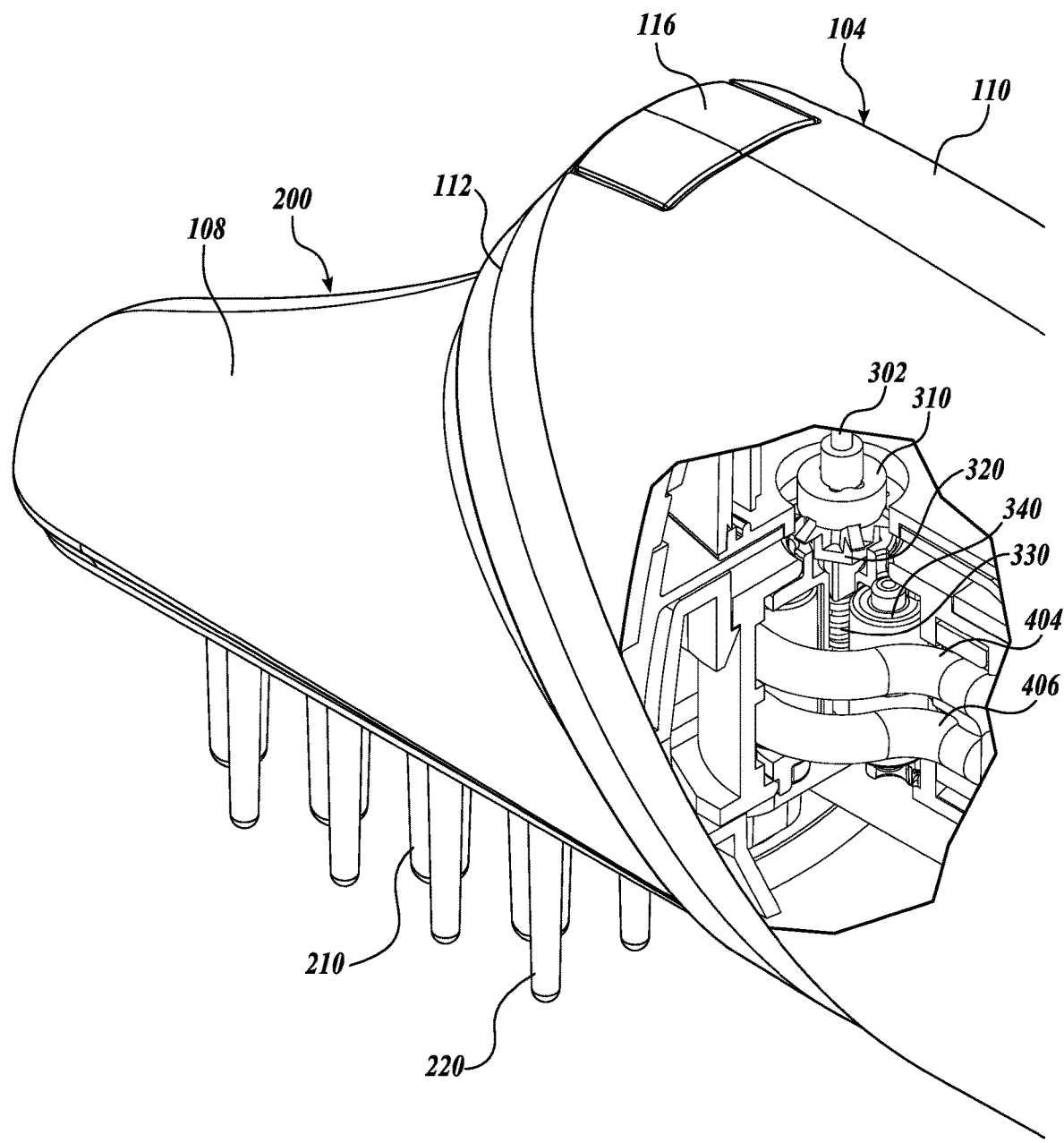
FIG. 5 is a partial cutaway window perspective view of the appliance of FIG. 1, showing components within the consumable assembly and the handle assembly.

Turning now to the partial cutaway view of the appliance 100 shown in FIG. 5, internal components of the appliance 100 configured for dispensing coloring formulation CF through the nozzles 210 will now be described. As shown, a first formulation tube 404 and a second formulation tube 406 are configured to transport one of the dye, developer, or other formulation from the fluid container 424 (see FIGS. 14A and 14B) to the manifold housing 202 for mixing and distribution to the nozzles 210. In other embodiments a single formulation tube or more than two formulation tubes are suitably used in the appliance 100. The first and second formulation tubes 404 and 406 are routed past a pump 340 consisting of a plurality of rollers to cause the coloring formulation CF to flow from the fluid container 424 to the manifold housing 202. In the illustrated embodiment, a peristaltic pump 340 is used. In this regard, one advantage of a peristaltic-type pump is that the pump is self-priming. However, in embodiments, any suitable pump, or series of pumps, is used to draw the coloring formulation CF from the fluid container 424 to the manifold housing 202.

The pump 340 is driven by a suitable a motor (not shown) disposed within the handle shell 110. The motor may rotationally drive the drive gear 310 through an elongate drive shaft 302. The drive gear 310 interfaces with a driven gear 320 configured to drive the various components of the appliance 100, including one or more of the pump 340 and a reciprocating wheel 206 (see FIG. 6, described in greater detail below), among other possible components. The interface of the drive gear 310 and the driven gear 320 is such that the gears 310 and 320 are capable of meshing by sliding together radially, e.g., in the direction in which the consumable assembly 200 is slid/inserted into the handle shell 110 during assembly of the appliance 100. The radial meshing of the gears 310 and 320 is accomplished by a biasing member shown as an axial spring 330 that is configured to allow the driven gear 320 to move axially away from the drive gear 310 during assembly of the appliance 100. The radial meshing of the gears 310 and 320 will be described in greater detail below. Although one example of radial meshing of the gears 310 and 320 is shown and described herein, other suitable gear meshing schemes are within the scope of the present disclosure.

The manifold housing 202 will now be described in greater detail. Turning to FIGS. 6-10, there is shown various cutaway views of the manifold housing 202 within the head cover 108. The plurality of nozzles 210 extend from a surface of the manifold housing 202 such that portions of the hair of a user pass between the plurality of nozzles 210 as the user passes the appliance 100 over the surface, e.g., the scalp. In some embodiments, the plurality of nozzles 210 is configured to reciprocate by reciprocation of the manifold housing 202 along the direction of the row of the plurality of nozzles 210. In this regard, the manifold housing 202 translates with respect to the head cover 108. The reciprocation of the nozzles 210 along the direction of the row allows the coloring formulation CF to cover areas of the surface between each of the nozzles 210 as the appliance 100 is passed over the surface in a direction perpendicular to the row of the plurality of nozzles 210. In this regard, the full surface below the plurality of nozzles 210 can be covered by the coloring formulation CF without having to overlap passes of the appliance 100 on the surface. In other embodiments, the nozzles 210 of the appliance are configured to oscillate, reciprocate along the length of the nozzles 210, vibrate, or remain stationary during use.

In one embodiment, the motion of the nozzles 210 is provided by the motor rotating the reciprocating wheel 206. The reciprocating wheel 206 includes a reciprocating protrusion 204 configured to interface with a reciprocating slot 208 in the manifold housing 202. As the reciprocating wheel 206 rotates, the reciprocating protrusion 204 translates within the reciprocating slot 208 in a direction across the body of the appliance 100 and therefore translates the manifold housing 202 in a direction along the body of the appliance 100. In some embodiments, the reciprocation has a frequency in the range of approximately 5-60 Hz, with an amplitude which is greater than one-half the distance between adjacent nozzles 210. In other embodiments, the amplitude of reciprocation of the manifold housing 202 is between about 0.5 times the distance between adjacent nozzles 210 and about 1.5 times the distance between adjacent nozzles 210. In other embodiments, any suitable arrangement for controlling the movement of the nozzles 210 is used. In another aspect, the movement of the nozzles 210 simulates the gloved finger rubbing the formulation into the root and hairline areas, resulting in an accurate control over the coloring for the hair areas.

The manifold housing 202 includes a plurality of chambers for the mixing, processing, and discharge control of the coloring formulation CF components from the formulation containers 424. For manufacturing and assembly purposes, the manifold housing 202 may include assembly aides, such as an assembly pin 218 and an assembly sleeve 216. In these embodiments, the assembly pin 218 is inserted into the assembly sleeve 216 to couple the components. In this regard, a press fit or an adhesive may be used to reinforce the coupling. Likewise, in other embodiments, a greater or a fewer number of pieces may be used to form and/or assemble the manifold housing 202.

In one aspect, the plurality of chambers of the manifold housing 202 are arranged and configured to provide an even discharge of the coloring formulation CF through each of the plurality of nozzles 210. In this regard, in some embodiments, the flow rate of the coloring formulation CF discharged from each of the plurality of nozzles 210 is within about 20% of the average flow rate of the coloring formulation CF from all of the plurality of nozzles 210. The flow rate control by the manifold housing 202 allows an even distribution of the coloring formulation CF to the surface. In other embodiments, the flow rate of the coloring formulation CF discharged from each of the plurality of nozzles 210 is within about 15% of the average flow rate of the coloring formulation CF from all of the plurality of nozzles 210. Still, in further embodiments, the flow rate of the coloring formulation CF discharged from each of the plurality of nozzles 210 is within about 10% of the average flow rate of the coloring formulation CF from all of the plurality of nozzles 210. In further embodiments, the flow rate of the coloring formulation CF discharged from each of the plurality of nozzles 210 is within about 5% of the average flow rate of the coloring formulation CF from all of the plurality of nozzles 210.

The chamber configuration of the manifold housing 202 suitable for controlling the mixing, processing, and discharging of the coloring formulation CF components from the formulation containers 424 will now be described in greater detail. Although the chamber configuration shown in the FIGURES is described below, it should be appreciated that the chamber configuration of the manifold housing 202 may instead have any suitable order or layout to accomplish the mixing and flow rate characteristics described above. In other embodiments, the mixing of the components of the coloring formulation CF occurs outside of the manifold housing 202, such as between the pump 340 and the inlets to the manifold housing 202.

Figure 6:
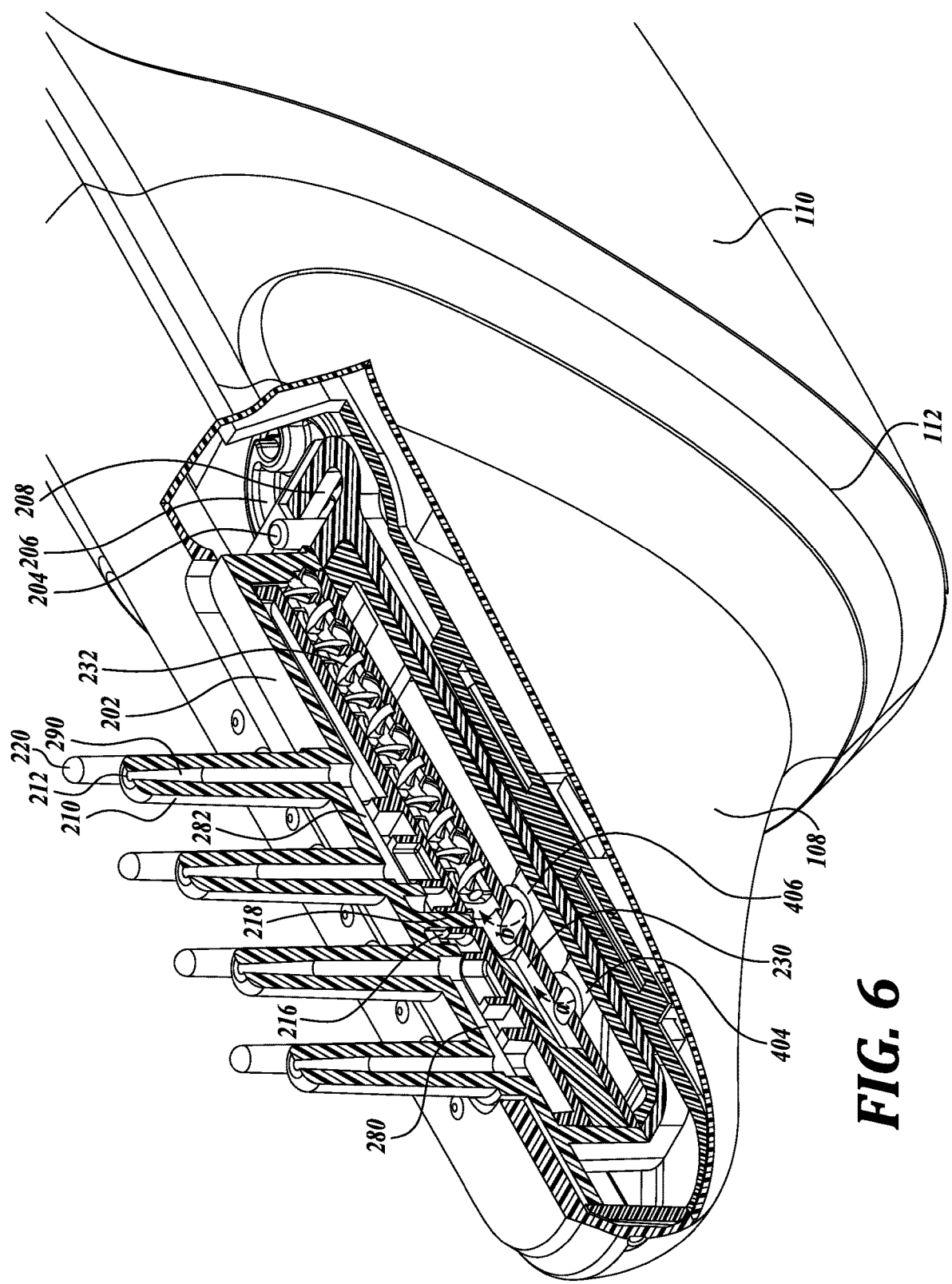
FIG. 6 is a partial cross-sectional perspective view of a manifold housing within a head cover of the consumable assembly of the appliance of FIG. 1.

Beginning with FIG. 6, there is shown a partial cross-sectional view of a portion of the chambers of the manifold housing 202. As noted above, the manifold housing 202 may receive the components of the coloring formulation CF from the first and second formulation tubes 404 and 406. In the illustrated embodiment, the components of the coloring formulation CF enter the manifold housing 202 at inlets a and b (see FIG. 7) and exit the manifold housing 202 at outlets h, i, j, and k (see FIG. 10). The flow of the components of the coloring formulation CF is detailed below.

Figure 7:
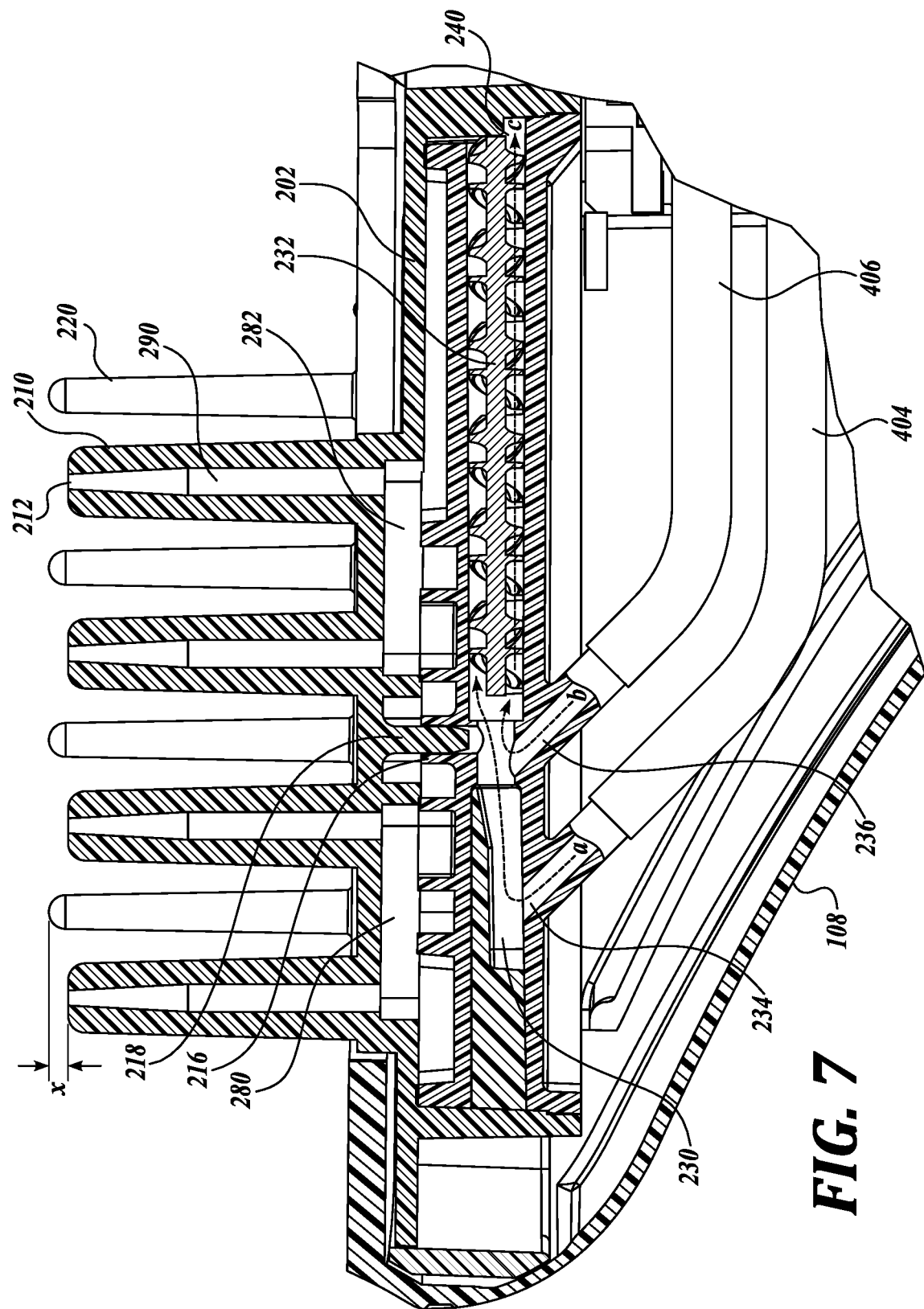
FIG. 7 is a cross-sectional side view of a portion of the consumable assembly taken along a line at substantially the midpoint of the width of the appliance of FIG. 1, showing the manifold housing within the head cover.

Turning to FIG. 7, which shows a side cross-sectional view taken along a line at substantially the midpoint of the width of the appliance 100, a first component of the coloring formulation CF flows through the first formulation tube 404 to the inlet flow point a, leading into a first chamber 230. Likewise, a second component of the coloring formulation CF flows through the second formulation tube 406 to the inlet flow point b, leading into the first chamber 230. Although not shown in the FIGURES, any number of inlets, such as a single inlet or more than two inlets, is also within the scope of the present disclosure. If using a developer or multiple colors of dye, prior to discharge of the coloring formulation CF through the outlet aperture 212, the components must be mixed together. Some mixing of the components of the coloring formulation CF may occur in the first chamber 230; however, for thorough mixing, the components flow toward a flow point c through a static mixer 232 to a second chamber 240. The flow through the static mixer 232 ensures the proper mixing of the components of the coloring formulation CF prior to the arrival of the components to the second chamber 240. As above, the mixed components will now be referred to generally as the coloring formulation CF.

Figure 8:
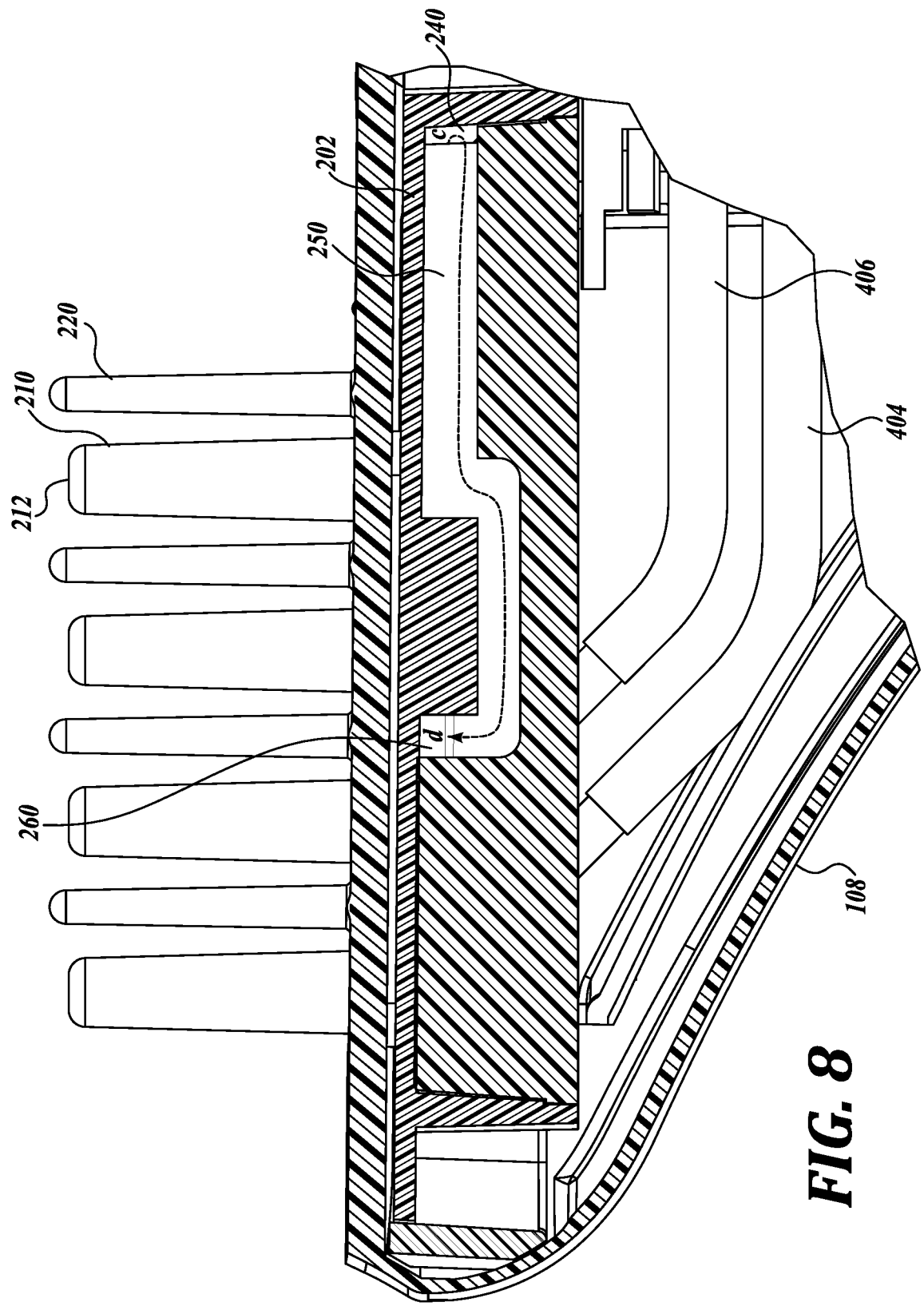
FIG. 8 is a cross-sectional side view of a portion of the consumable assembly taken along a line offset from the midpoint of the width of the appliance of FIG. 1, showing the manifold housing within the head cover.
Figure 9:
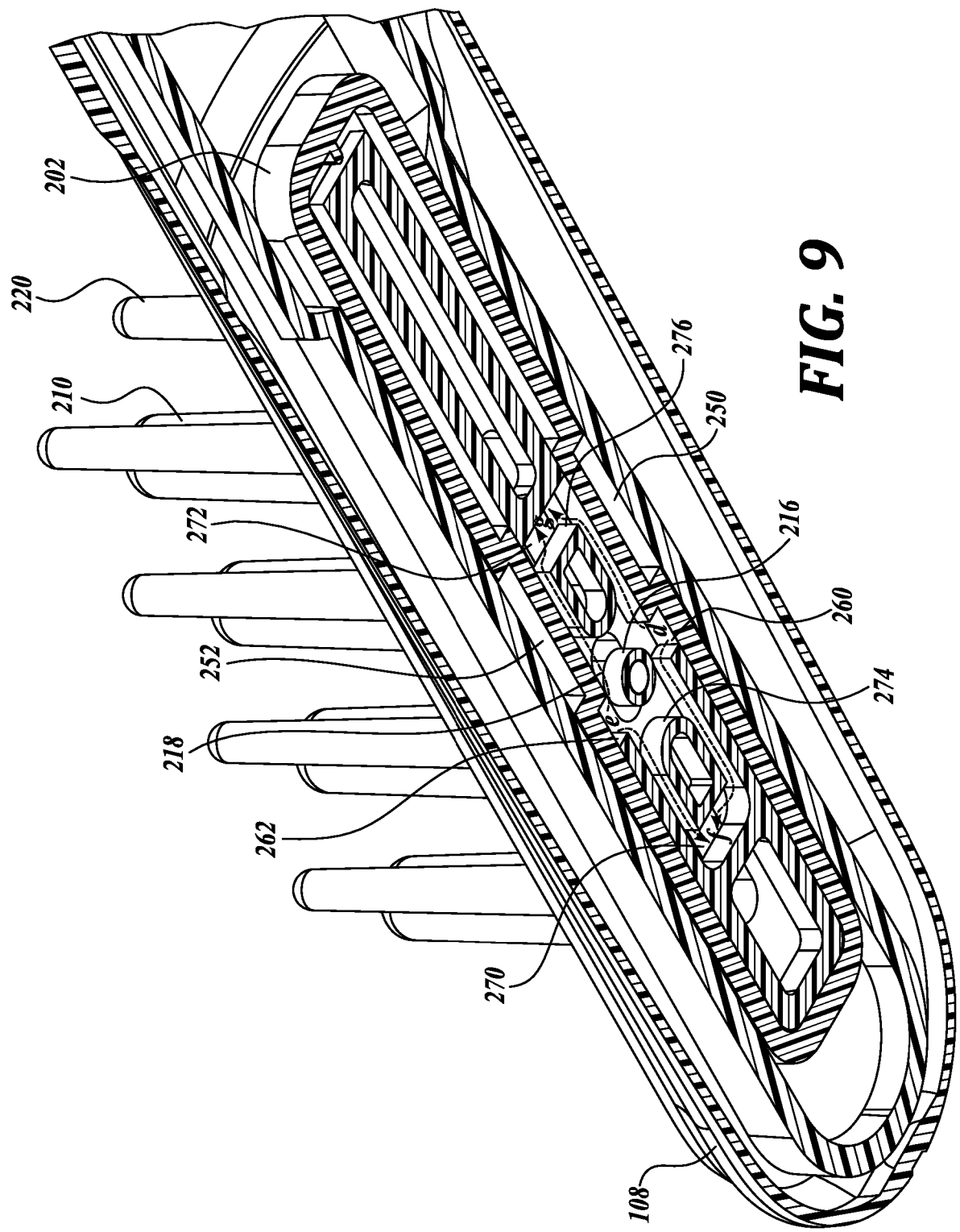
FIG. 9 is a cross-sectional perspective view of a portion of the consumable assembly taken along a line at an intermediate point along the height of the appliance of FIG. 1, showing the manifold housing within the head cover.

Turning to FIG. 8, which shows a side cross-sectional view take along a line offset from the midpoint of the width of the appliance 100 (outwardly from the page), the flow of the coloring formulation CF is continued from the second chamber 240, into a third chamber 250. The third chamber 250 is mirror symmetrical with an identical chamber 252 (partially shown in FIG. 9) on the opposite side of the manifold housing 202, such that the flow of the coloring formulation CF splits at the flow point c in the second chamber 240 into two separate passageways: the third chamber 250 and the mirror symmetrical chamber 252 on the opposite side of the manifold housing 202. The coloring formulation CF continues to flow from the third chamber 250 to a flow point d at a fourth chamber 260. As can be seen in FIG. 9, the mirror symmetrical path flows from the flow point c through the mirror symmetrical third chamber 252 to a flow point e at a mirror symmetrical fourth chamber 262.

Turning to FIG. 9, which shows a side cross-sectional view taken along a line at an intermediate point along the height of the appliance 100 perpendicular to the cross-sectional cuts shown in FIGS. 6-8, the flow of the coloring formulation CF at a flow point d and a flow point e is further split into dual flow paths toward a flow point f and a flow point g at a fifth chamber 270 and a sixth chamber 272, respectively. The flow of the coloring formulation CF is split at the flow point d and the flow point e such that the coloring formulation CF at the flow point f contains fluid from both the fourth chamber 260 and the mirror symmetrical fourth chamber 262. Likewise, the coloring formulation CF at the flow point g contains fluid from both the fourth chamber 260 and the mirror symmetrical fourth chamber 262.

As the coloring formulation CF flows from the flow points d and e to the flow point f, the coloring formulation CF travels around a first distribution protrusion 274. Similarly, as the coloring formulation CF flows from the flow points d and e to the flow point g, the coloring formulation CF travels around a second distribution protrusion 276. In some embodiments, the first and second distribution protrusions 274 and 276 help to ensure an even flow rate of fluid at the fifth and sixth chambers 270 and 272, such that the discharge from the nozzles 210 is evenly distributed, as described above.

Figure 10:
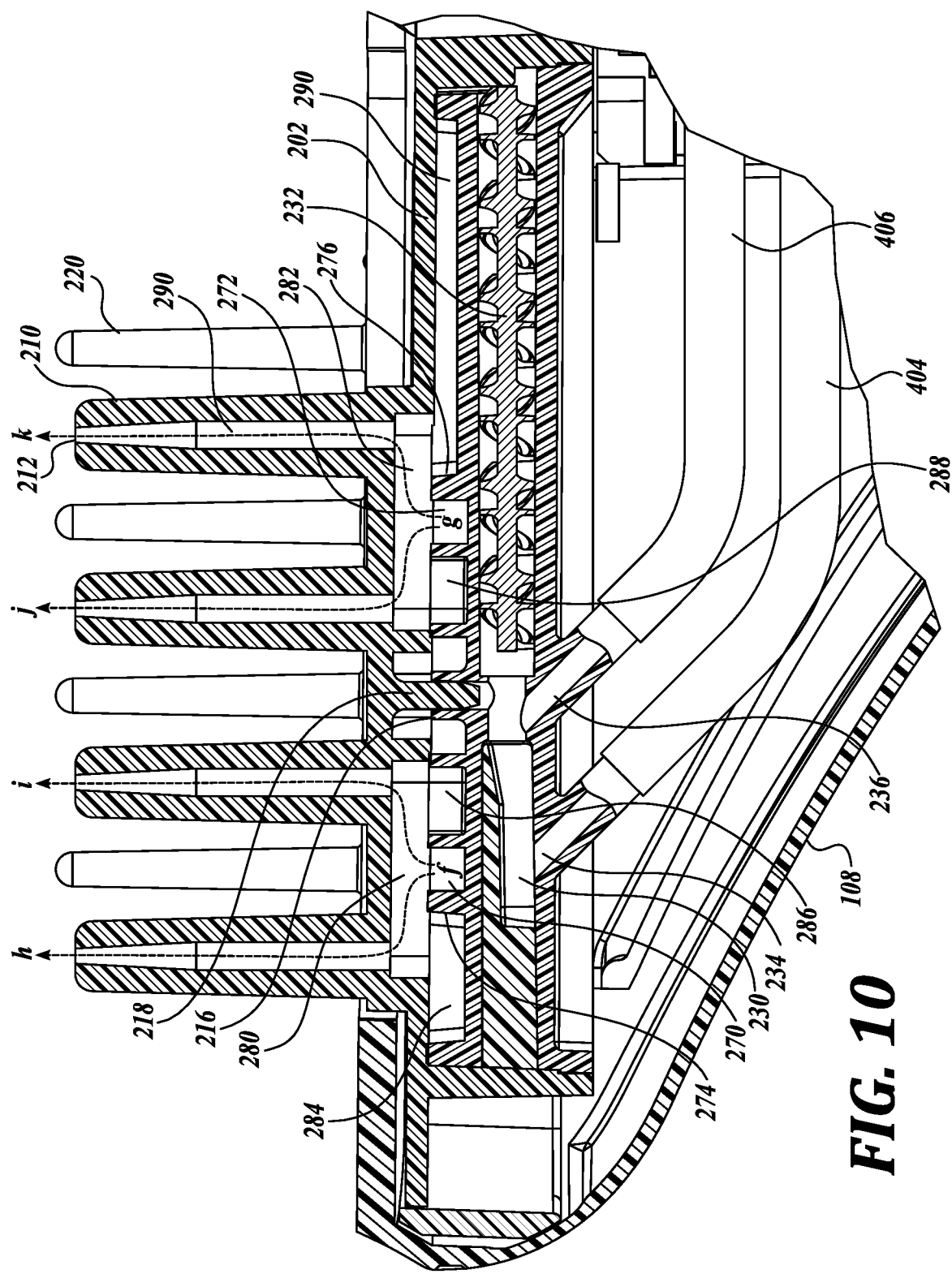
FIG. 10 is a cross-sectional side view of a portion of the consumable assembly taken along a line at substantially the midpoint of the width of the appliance of FIG. 1, showing the manifold housing within the head cover.

Turning to FIG. 10, which shows a partial side cross-sectional view taken along a line at substantially the midpoint of the width of the appliance 100 (as in FIG. 6), the flow of the coloring formulation CF at the flow points f and g travels into a seventh chamber 280 and an eighth chamber 282, where the flow is further split into dual flow paths, each of the seventh and eighth chambers 280 and 282 acting as a plenum having two outlets into the nozzles 210. The flow at the seventh chamber 280 travels from the flow point f toward a discharge point h and a discharge point i at the outlet aperture 212, into a nozzle chamber 292 in each of the plurality of nozzles 210. Likewise, the flow at the eighth chamber 282 travels from the flow point g toward a discharge point j and a discharge point k at the outlet aperture 212, into the nozzle chamber 292 in each of the plurality of nozzles 210. As described above, the flow rate of the coloring formulation CF at each discharge point h, i, j, and k from each of the plurality of nozzles 210 may be within a specified percentage of the average flow rate of the coloring formulation CF from all of the plurality of nozzles 210.

Adjacent to the seventh chamber 280 are first and second volume chambers 284 and 286, and adjacent to the eighth chamber 282 are third and fourth volume chambers 288 and 290. The volume chambers 284, 286, 288, and 290 provide a location for fluid expansion, e.g., from the expanding effects of an optional heat source applied to the coloring formulation CF (described in greater detail below), fluid vibration reduction, additional ballast volume to ensure steady discharge of the coloring formulation CF, and the like.

As noted above, in some embodiments, an energy source, (e.g., a heat source, not shown) may be added to any location in the path of the coloring formulation CF flow to raise the temperature of the formulation, or it may be added to the appliance 100 such that the heat is transferred to the application surface, e.g., the scalp. In this regard, for certain formulations, it may be beneficial in either user comfort, formulation efficacy, or both, to apply the formulation to the user at an elevated temperature, or to heat the application surface. In these embodiments, the heat source is configured to deliver energy to the formulation or the application surface. In some embodiments, the energy source is an ultraviolet radiation source configured to illuminate the plurality of nozzles 210 to transfer ultraviolet radiation to the application surface, such as to hair roots and/or scalp tissue. In other embodiments, the energy source is a heat source configured to heat the formulation prior to discharge from the plurality of outlet nozzles 210.

Turning now to FIGS. 11A-12D, the selectively engaging coupling of the drive gear 310 and the driven gear 320 will now be described in greater detail. To drive the pump 340, the reciprocation of the manifold housing 202 and any other suitable system of the appliance 100, one or more motors may be provided in the handle assembly 104, as noted above. In other embodiments, the motor may be included in the consumable assembly 200; however, the consumable assembly 200 is intended to be disposable and replaced after a specified duration of use. In embodiments where the motor is located in the handle assembly 104, a selectively engaging coupling having a biasing member is included to allow the meshing of the drive gear 310 and the driven gear 320.

In general, the coupling is configured to allow meshing of the drive gear 310 and the driven gear 320 when the consumable assembly 200 is slid/inserted into the handle assembly 104. More specifically, the coupling allows drive gear 310 and the driven gear 320 to slide radially relative to one another from a non-engagement position, where the consumable assembly 200 is not yet seated within the handle assembly 104, to an engagement position, where the consumable assembly 200 is fully inserted within the handle assembly 104 and the axes of the drive gear 310 and the driven gear 320 are substantially aligned such that the drive gear 310 may be configured to transfer rotational motion to the driven gear 320.

The components of the drive gear 310 and the driven gear 320 will now be described in greater detail. As described above, the drive gear 310 is driven rotationally by the motor through the elongate drive shaft 302, which defines a drive axis. In some embodiments, the drive gear 310 may include a drive sleeve 312 to provide a reinforced coupling of the drive gear 310 to the elongate drive shaft 302. Similarly, the driven gear 320 is driven rotationally by the drive gear 310 such that the driven gear causes an elongate driven shaft 332 to rotate. The elongate driven shaft 332 defines a driven axis. In some embodiments, the driven gear 320 may include a driven sleeve 322 to provide a reinforced coupling of the driven gear 320 to the driven shaft 332.

Figure 11B:
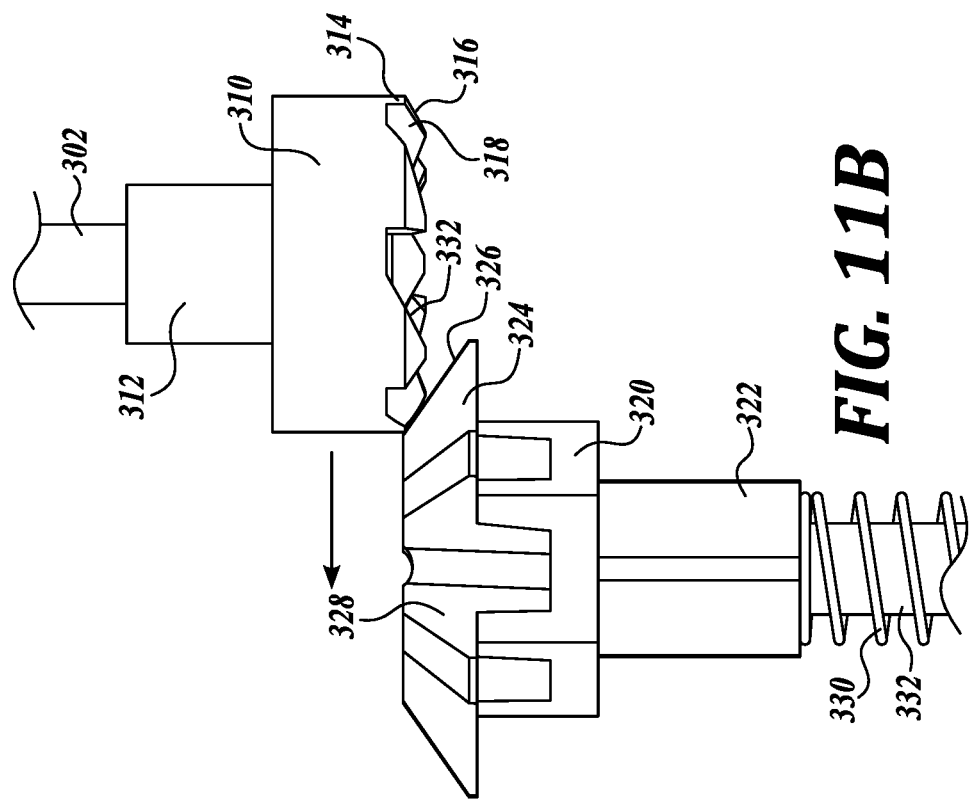
Figure 11A:
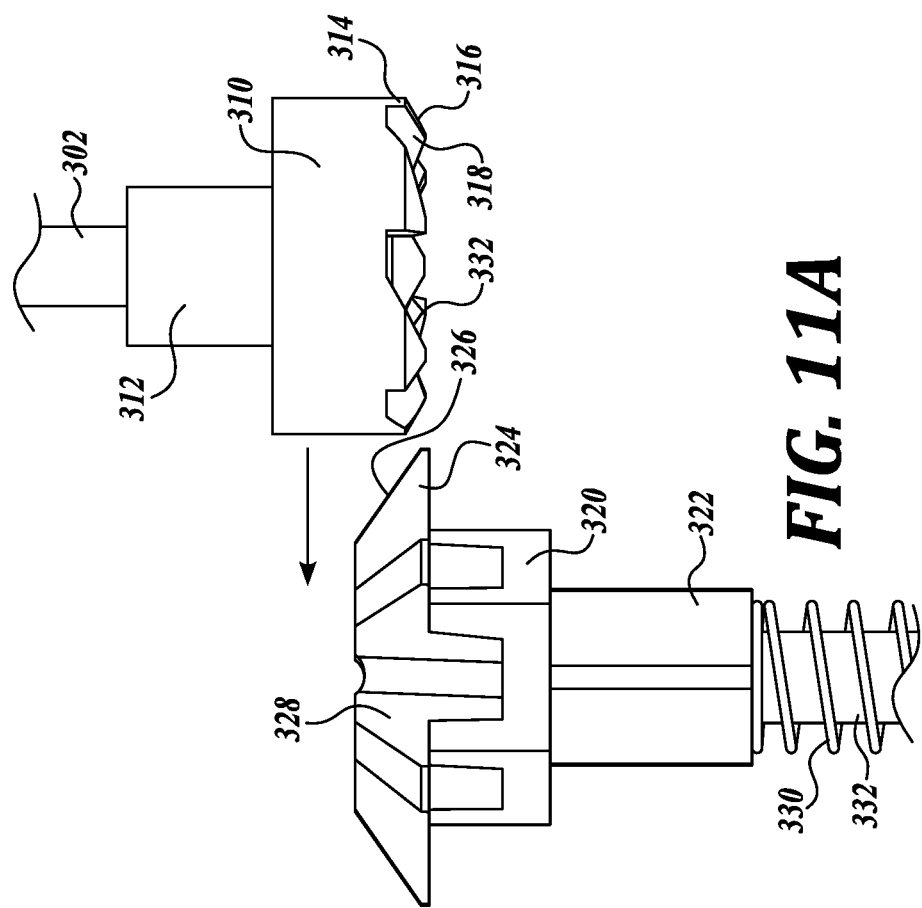

As described briefly above, the radial sliding and meshing of the gears 310 and 320 is accomplished by the biasing member, shown as the axial spring 330, where the biasing member is configured to allow the driven gear 320 to move axially away from the drive gear 310 during assembly of the consumable assembly 200 into the handle assembly 104. The radial sliding of the gears 310 and 320 from the non-engagement position (FIG. 11A) to the engagement position (FIG. 11E) is accomplished by interface of a drive tooth 314 of the drive gear 310 with driven tooth 324 of the driven gear 320. In the illustrated embodiment, the drive tooth 314 includes a first ramp 316 configured to engage a second ramp 326 of the driven tooth 324. As a result of the radial sliding of the drive gear 310 and the driven gear 320, the first ramp 316 interfaces the second ramp 326 (FIG. 11B). As the drive gear 310 is slid radially toward the engagement position, the interface of the first ramp 316 and the second ramp 326 urges the driven gear 320 axially away from the drive gear 310 (FIG. 11C), compressing the axial spring 330 and allowing the drive gear 310 to continue to radially slide toward the engagement position.

As the drive gear 310 approaches the engagement position, the axial spring 330 urges the driven gear 320 axially toward the drive gear 310 to initiate engagement of the drive tooth 314 and the driven tooth 324 (FIG. 11D). As the drive gear 310 is rotated while the gears 310 and 320 are in the engagement position (FIG. 11E), a drive tooth engagement face 318 of the drive gear 310 abuts a driven tooth engagement face 328 of the driven gear 320 such that the rotational motion of the drive gear 310 is transferred to the driven gear 320, driving the components of the appliance 100. In the illustrated embodiment, the drive gear 310 engages the driven gear 320 in a single rotational direction. However, in other embodiments, the drive gear 310 is configured to engage the driven gear 320 in both rotational directions.

Figure 12A:
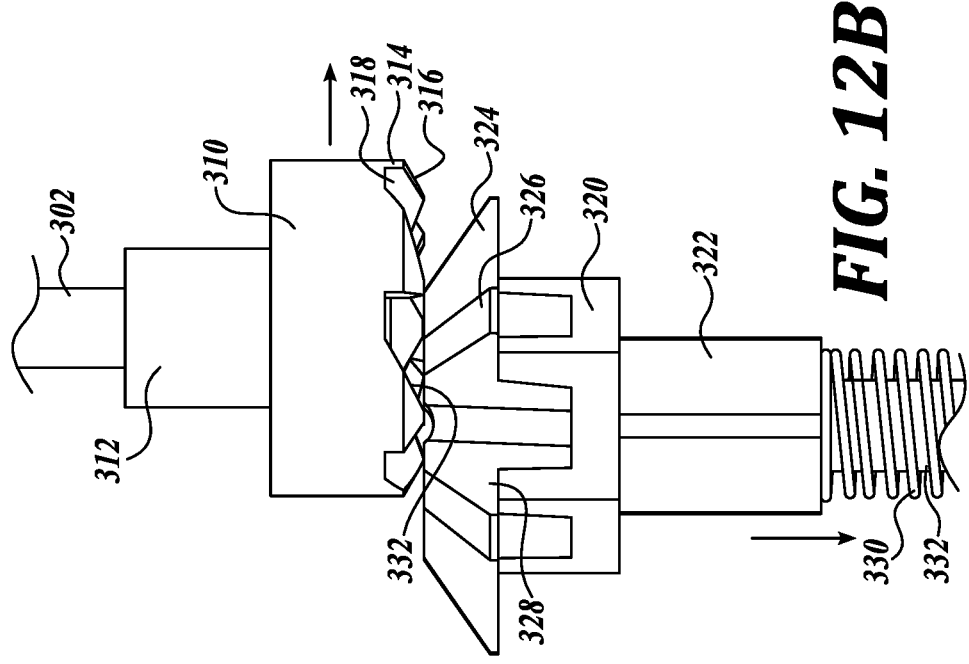
Figure 12B:
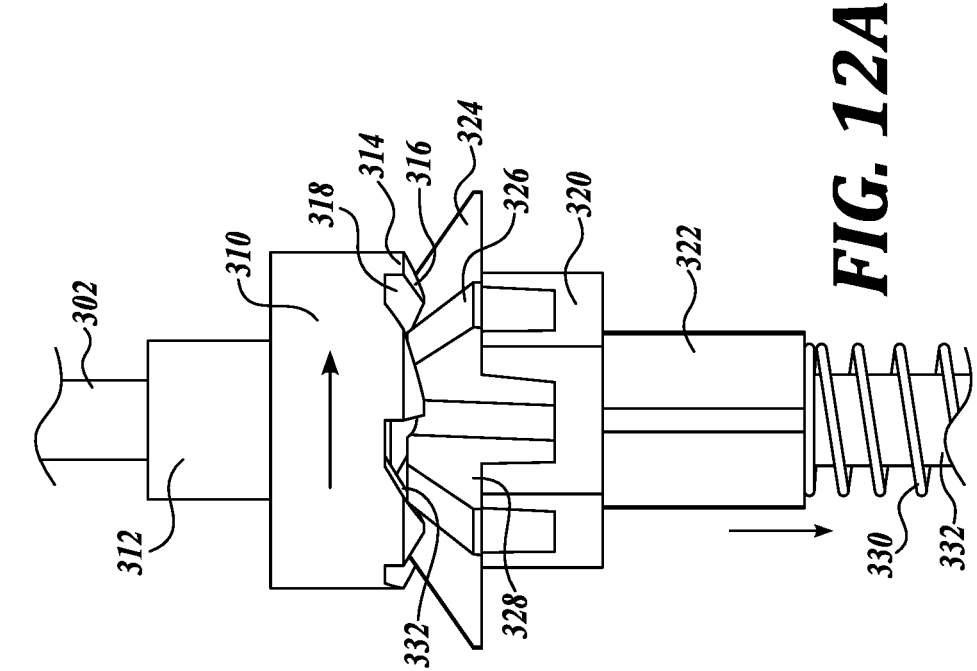

Upon disassembly of the consumable assembly 200 from the handle assembly 104, the selective engagement coupling of the drive gear 310 and the driven gear 320 must necessarily be released. As the drive gear 310 is slid radially from the engagement position (FIG. 12A) to the non-engagement position (FIG. 12D), a cam member 332 of the drive tooth 314 engages the driven tooth 324 to again urge the driven gear 320 axially away from the drive gear 310 (FIG. 12B). As the drive gear 310 is slid radially away from the engagement position, the interface of the cam member 332 and the driven tooth 324 compresses the axial spring 330, allowing the drive gear 310 to continue to radially slide away from the engagement position. In some embodiments, the cam member 332 additionally provides an urging of the drive tooth engagement face 318 toward the driven tooth engagement face 328, for example, in the transition from the configuration shown in FIG. 11D to the configuration shown in FIG. 11E. As the drive gear 310 continues to slide radially away from the engagement position, the first ramp 316 and the second ramp 326 again interface (FIG. 12C), allowing the axial spring 330 to urge the driven gear 320 axially toward a neutral point at the non-engagement position (FIG. 12D).

The fluid connection of the fluid containers 424 (hereinafter referred to as packets 424, see also the hair color packets described in detail in U.S. patent application Ser. Nos. 14/572,250 and 14/554,789, both of which are incorporated by reference herein) upon assembly of the consumable assembly 200 to the handle assembly 104 will now be described in detail. In some embodiments, the consumable assembly 200 includes one or more color packets 424 and a developer packet (not shown, but similar in appearance and function to color packet 424); however, in other embodiments, a single hair coloring packet 424 is suitably used. The use of a developer with the coloring dye formulation provides a more lasting coloring effect, up to about one month. The combination of coloring dye and developer is generally referred to as permanent coloring, while applying a dye without use of the developer results in a semi-permanent coloring, usually lasting about a week. The developer can be used with multiple coloring packets 424 or with a single coloring packet 424. The outlet of the coloring packet 424 and developer packet may be in fluid communication with the first formulation tube 404 and the second formulation tube 406, respectively. In this regard, the pump 340 creates a suction to draw fluid from the packets 424 into the first and second formulation tubes 404 and 406, such that the coloring formulation CF components travel through the first and second formulation tubes 404 and 406 and thereinafter into the manifold housing 202 at the flow points a and b.

Turning now to FIGS. 13A-14B, in some embodiments, the consumable assembly 200 is configured for disposal after a specified duration of use, e.g., after a single application of coloring formulation CF to the user's hair. In these embodiments, the consumable assembly 200 is removed from the handle assembly 104 for disposal, and a new consumable assembly 200 is installed into the handle assembly 104 for further use. For retail purposes, packets 424 of the consumable assembly 200 are initially sealed by a sealing member 420 such that coloring dye and/or developer do not leak out of the packet 424 and contaminants do not enter the packets 424. In some embodiments, the sealing member 420 includes an orifice 428 to establish fluid communication between the packet 424 and the formulation tubes 404 and 406 when connected. In other embodiments, the sealing member 420 is pierceable, such that the sealing member 420 is punctured when connected to establish fluid communication between the packet 424 and the formulation tubes 404 and 406 (as will be described in greater detail below). In the pierceable embodiments, the sealing member 420 is a one or two-way breathable membrane 426 configured to allow outgassing of the packet 424 without the ingress of contaminants or the egress of the contents of the packet 424. Still, in further embodiments, the sealing member 420 includes a valve (not shown), used in conjunction with any of the embodiments herein, the valve configured to regulate the flow of the fluid from the packets 424. Any combination of the above features may also be used.

Figure 13A:
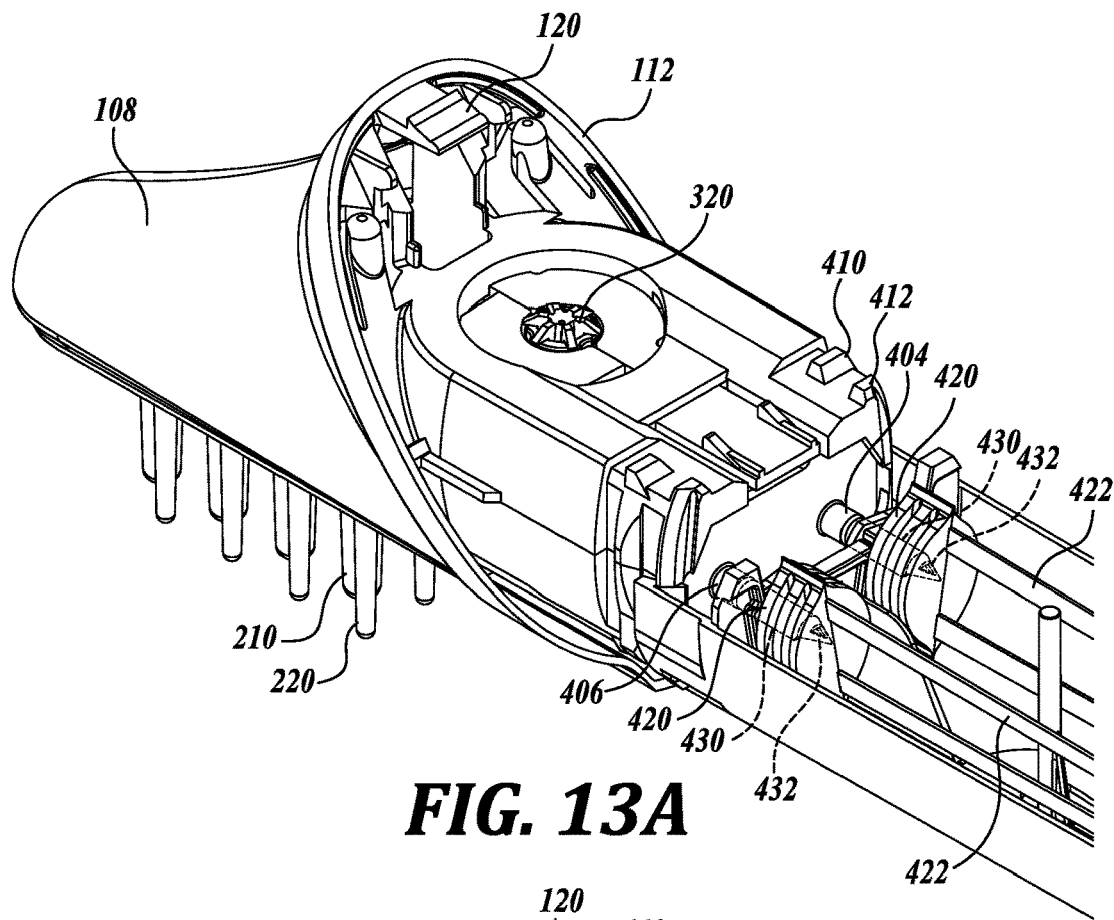
FIG. 13A is a perspective view of a portion of the consumable assembly of the appliance of FIG. 1, showing the consumable assembly in a sealed configuration.
Figure 13B:
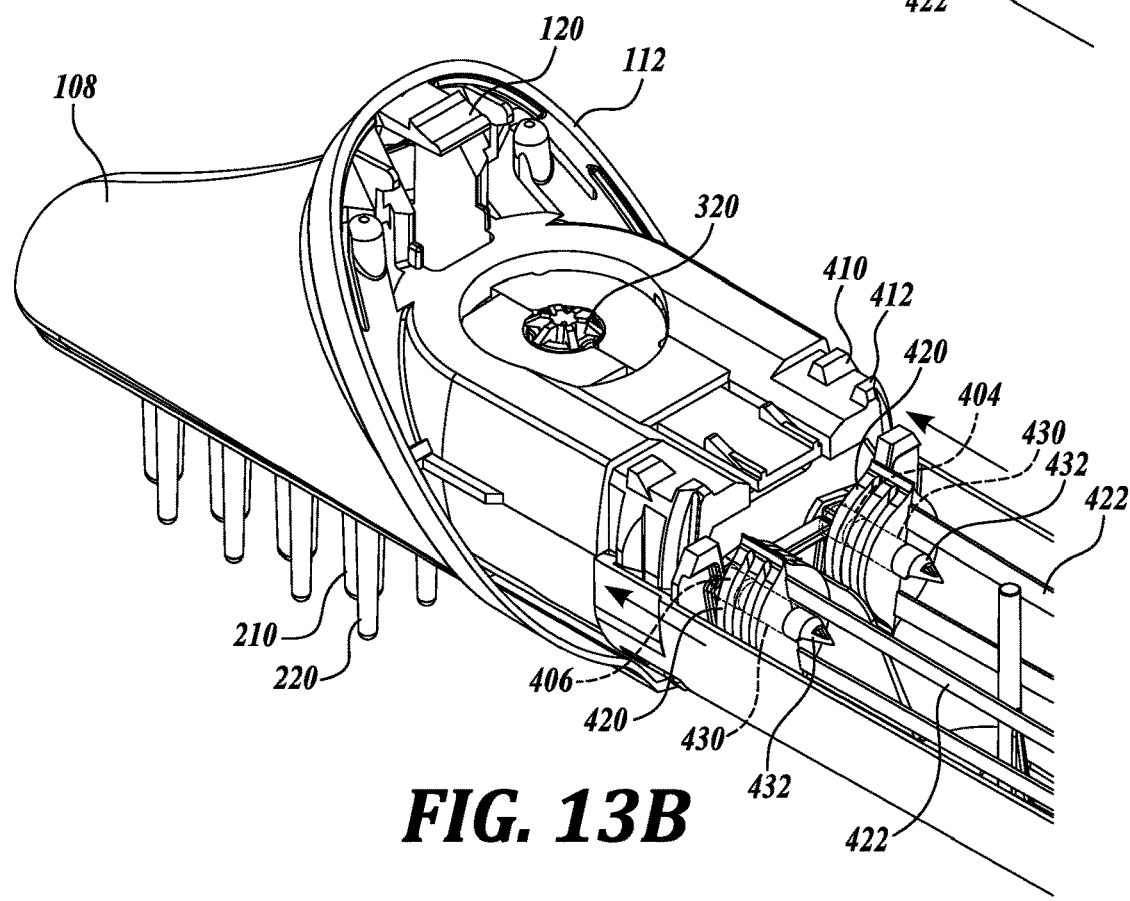
FIG. 13B is a perspective view of a portion of the consumable assembly of the appliance of FIG. 1, showing the consumable assembly in a fluid flow configuration.
Figure 14A:
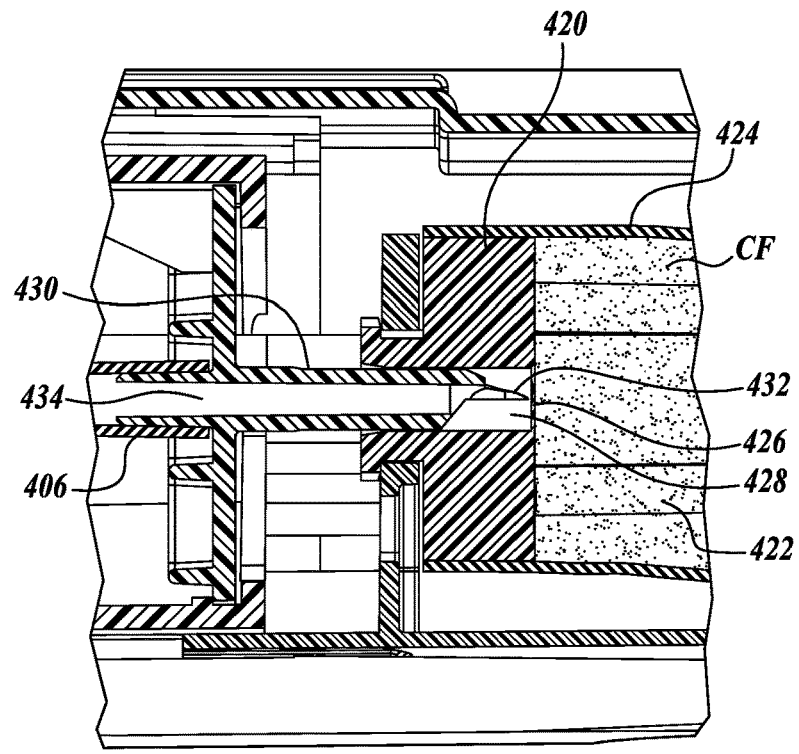
FIG. 14A is a side view of a portion the consumable assembly of the appliance of FIG. 1, showing the consumable assembly with coloring formulation in the sealed configuration.
Figure 14B:
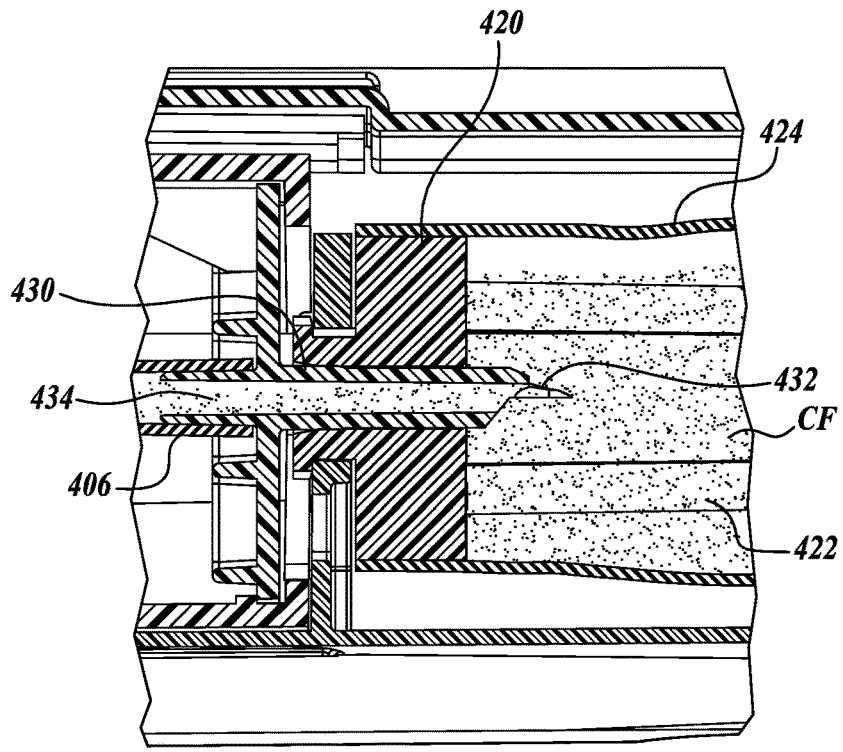
FIG. 14B is a side view of a portion the consumable assembly of the appliance of FIG. 1, showing the consumable assembly with coloring formulation in the fluid flow configuration.

In the illustrated embodiment, when the consumable assembly 200 is inserted into the handle assembly 104, the consumable assembly 200 transitions from a sealed configuration, where the sealing member 420 is intact (see FIGS. 13A and 14A), to a fluid flow configuration, where the sealing member 420 has been opened to establish fluid communication between the packet 424 and the formulation tubes 404 and 406 (see FIGS. 13B and 14B). In embodiments where the sealing member 420 is pierceable (such as by using the membrane 426), the ends of the formulation tubes 404 and 406 include a piercing portion 430 having a piercing tip 432 to puncture the sealing member 420 upon installation of the consumable assembly 200 within the handle assembly 104.

The piercing portion 430 defines a fluid receiving chamber 434 therein to receive the fluid and fluidly connect the packet 424 to the formulation tubes 404 and 406. In some embodiments, the packets 424 are enclosed in a packet housing 402 (see FIG. 4). In these embodiments, the packet housing 402 includes two positions corresponding to the sealed configuration and the fluid flow configuration.

As shown in FIG. 13A, the consumable assembly 200 includes a sealed packet detent 412 and a fluid flow packet detent 410 positioned further toward the head cover 108 end of the appliance 100. The position of the detents 412 and 410 correspond to the sealed configuration, where an aperture 408 of the packet housing 402 engages the sealed packet detent 412 such that the piercing tip 432 does not puncture the sealing member 420, and the fluid flow configuration, where the aperture 408 engages the fluid flow packet detent 410 such that the piercing tip 432 punctures the sealing member 420 (in the position as shown in FIG. 4).

In the sealed configuration of FIGS. 13A and 14A, such as when the consumable assembly 200 is stored and purchased at retail, the sealing member 420 has not yet been pierced. In this configuration, the aperture 408 engages the sealing packet detent 412. As the consumable assembly 200 is inserted into the handle assembly 104, a portion of the packet housing 402 abuts a portion of the handle assembly 104 such that the packet housing 402 transitions to the fluid flow packet detent 410. More specifically, the packet housing 402 slides forward toward the head cover 108 (in the direction of the arrows in FIG. 13B), and the piercing tip 432 of the piercing portion 430 punctures the sealing member 420 (e.g., the membrane 426). Upon complete installation of the consumable assembly 200 to the handle assembly 104, the aperture 408 engages the fluid flow packet detent 410 to keep the packets 424 in sealed fluid communication with the formulation tubes 404 and 406 during use of the appliance 100.

In embodiments where the packets 424 include flexible walls, the consumable assembly 200 includes packet flow protrusions 422 extending along the length of the packet to prevent premature sealing of the remaining fluid within the packet 424 as the packet walls collapse, which would otherwise restrict the flow of fluid into the formulation tubes 404 and 406, preventing the full use of the entire volume of formulation within the packets 424.

The detailed description set forth above in connection with the appended drawings, where like numerals reference like elements, are intended as a description of various embodiments of the present disclosure and are not intended to represent the only embodiments. Each embodiment described in this disclosure is provided merely as an example or illustration and should not be construed as preferred or advantageous over other embodiments. The illustrative examples provided herein are not intended to be exhaustive or to limit the disclosure to the precise forms disclosed. Similarly, any steps described herein may be interchangeable with other steps, or combinations of steps, in order to achieve the same or substantially similar result.

In the foregoing description, specific details are set forth to provide a thorough understanding of exemplary embodiments of the present disclosure. It will be apparent to one skilled in the art, however, that the embodiments disclosed herein may be practiced without embodying all of the specific details. In some instances, well-known process steps have not been described in detail in order not to unnecessarily obscure various aspects of the present disclosure. Further, it will be appreciated that embodiments of the present disclosure may employ any combination of features described herein.

The present application may include references to directions, such as "forward," "rearward," "front," "back," "upward," "downward," "right hand," "left hand," "lateral," "medial," "in," "out," "extended," "advanced," "retracted," "proximal," "distal," "central," etc. These references, and other similar references in the present application, are only to assist in helping describe and understand the particular embodiment and are not intended to limit the present disclosure to these directions or locations.

The present application may also reference quantities and numbers. Unless specifically stated, such quantities and numbers are not to be considered restrictive, but exemplary of the possible quantities or numbers associated with the present application. Also in this regard, the present application may use the term "plurality" to reference a quantity or number. In this regard, the term "plurality" is meant to be any number that is more than one, for example, two, three, four, five, etc. The term "about," "approximately," etc., means plus or minus 5% of the stated value.

The principles, representative embodiments, and modes of operation of the present disclosure have been described in the foregoing description. However, aspects of the present disclosure, which are intended to be protected, are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure as claimed.

The embodiments of the invention in which an exclusive property or privilege is claimed are defined as follows:

1. A formulation delivery system, comprising:
   a first fluid container configured to retain a volume of a first formulation;
   a first fluid receiving chamber having an inlet member, the first fluid container removably couplable to the first fluid receiving chamber such that upon coupling, the inlet member interfaces with an orifice of the first fluid container to allow regulated flow of the first formulation from the first fluid container to the first fluid receiving chamber, the first fluid receiving chamber being in fluidic connection with a first formulation tube;
   a second fluid receiving chamber configured to receive a second formulation from a second fluid container, the second fluid receiving chamber being in fluidic connection with a second formulation tube that is fluidically parallel to the first formulation tube; and
   a manifold connected in parallel to the first formulation tube and to the second formulation tube and comprising a first chamber and a mixing chamber, wherein the first formulation tube and the second formulation tube fluidically connect to the first chamber upstream of the mixing chamber, wherein the mixing chamber is configured to mix the first formulation with the second formulation into a mixed formulation, and wherein a first flow point of the manifold downstream of the mixing chamber splits the mixed formulation into a first flow path and a second flow path, wherein at least one of the first flow path or the second flow path includes a portion which is not parallel to a longitudinal axis of the mixing chamber.

2. The formulation delivery system of claim 1, wherein a second flow point downstream of the first flow point further splits the mixed formulation into a third flow path and a fourth flow path.

3. The formulation delivery system of claim 2, wherein a third flow point downstream of the first flow point further splits the mixed formulation into a fifth flow path and a sixth flow path.

4. The formulation delivery system of claim 1, further comprising a membrane covering the orifice, wherein the membrane is pierceable by the inlet member upon coupling of the first fluid container to the first fluid receiving chamber.

5. The formulation delivery system of claim 1, wherein the first fluid container further comprises a valve configured to regulate the flow of the first formulation out of the orifice.

6. The formulation delivery system of claim 1, wherein the orifice is closed until the first fluid container is coupled to the fluid receiving chamber.

7. The formulation delivery system of claim 6, wherein the first fluid container further comprises a membrane covering the orifice that is configured to allow outgassing of the first formulation while substantially preventing the flow of first formulation from the first fluid chamber.

8. The formulation delivery system of claim 1, wherein the first fluid container includes a flexible wall that at least partially collapses as the first formulation flows from the fluid chamber, wherein the first fluid container includes a protrusion extending through the length of the first fluid container, the protrusion configured to create a flow path for the first formulation as the flexible wall at least partially collapses.

9. The formulation delivery system of claim 8, further comprising a motorized pump disposed along the first formulation tube and the second formulation tube.

10. The formulation delivery system of claim 1, wherein the first fluid container includes a container shape that mates with a correspondingly shaped area of a housing for the first fluid container.

11. The formulation delivery system of claim 10, wherein the first fluid container includes a flat wall such that the first fluid container is rotationally oriented when inserted into the housing.

12. The formulation delivery system of claim 1, wherein the first fluid container includes a first internal bladder configured to retain the first formulation.

13. The formulation delivery system of claim 1, wherein the mixing chamber comprises a static mixer disposed therein.

14. The formulation delivery system of claim 1, wherein the first fluid receiving chamber is configured to withdraw the first formulation from the first fluid container.

15. The formulation delivery system of claim 1, wherein the first formulation is selected from the group consisting of permanent hair dye, semi-permanent hair dye, developer, conditioner, hair growth treatment, ROGAINE®, hair protein treatment, fluid hair treatment, and fluid scalp treatment.

16. A hair and scalp formulation delivery system, comprising:
   a fluid container configured to retain a volume of formulation;
   a fluid receiving chamber having an inlet member, the fluid container removably couplable to the fluid receiving chamber such that upon coupling, the inlet member interfaces with an orifice of the fluid container to allow flow of the formulation from the fluid container to the fluid receiving chamber;
   a motorized pump in fluid communication with the fluid receiving chamber to withdraw the formulation from the fluid container; and
   a reciprocating formulation delivery nozzle in fluid communication with the motorized pump, the reciprocating formulation delivery nozzle being coupled to a motor and configured to discharge the formulation from the delivery system while reciprocating.

17. The hair and scalp formulation delivery system of claim 16, further comprising a membrane covering the orifice.

18. The hair and scalp formulation delivery system of claim 17, wherein the membrane is pierceable by the inlet member upon coupling of the fluid container to the fluid receiving chamber.

19. The hair and scalp formulation delivery system of claim 16, wherein the reciprocating formulation delivery nozzle is coupled to the motor by a reciprocating wheel.

20. The hair and scalp formulation delivery system of claim 16, wherein the orifice is closed such that the formulation is retained within the fluid container until the fluid container is coupled to the fluid receiving chamber.

21. The hair and scalp formulation delivery system of claim 20, wherein the fluid container further comprises a membrane covering the orifice that is configured to allow outgassing of the formulation while substantially preventing the flow of formulation from the fluid chamber.

22. The hair and scalp formulation delivery system of claim 16, wherein the motor drives the motorized pump.

23. The hair and scalp formulation delivery system of claim 22, wherein the fluid container includes a flat wall such that the fluid container is rotationally oriented when inserted into the housing.

24. The hair and scalp formulation delivery system of claim 16, wherein the formulation is selected from the group consisting of permanent hair dye, semi-permanent hair dye, developer, conditioner, hair growth treatment, ROGAINE®, hair protein treatment, fluid hair treatment, and fluid scalp treatment.

* * * * *